(12) United States Patent
Diefenbach et al.

(10) Patent No.: US 6,559,144 B2
(45) Date of Patent: May 6, 2003

(54) BICYCLIC AMINO ACIDS

(75) Inventors: Beate Diefenbach, Darmstadt (DE); Simon L. Goodman, Darmstadt (DE); Joachim März, Gross-Gerau (DE); Peter Raddatz, Seeheim (DE); Friedrich Rippmann, Heidelberg (DE); Matthias Wiesner, Mainz (DE)

(73) Assignee: Merck Patent Gesellschaft Mit, Darmstadt (DE)

( * ) Notice: Subject to any disclaimer, the term of this patent is extended or adjusted under 35 U.S.C. 154(b) by 0 days.

(21) Appl. No.: 09/842,004

(22) Filed: Apr. 26, 2001

(65) Prior Publication Data

US 2001/0021709 A1 Sep. 13, 2001

Related U.S. Application Data

(62) Division of application No. 09/367,219, filed as application No. PCT/EP98/00636 on Feb. 6, 1998, now abandoned.

(30) Foreign Application Priority Data

Feb. 13, 1997 (DE) .......................... 197 05 450

(51) Int. Cl.$^7$ ................... A61K 31/536; A61K 31/357; C07D 319/14; C07D 215/00; C07D 365/34

(52) U.S. Cl. ................... 514/231.2; 514/311; 514/312; 514/315; 514/456; 514/452; 544/49; 544/106; 544/349; 544/353; 546/152; 546/153; 549/357; 549/377

(58) Field of Search ................ 514/311, 452, 514/456, 312, 315, 231.2, 313; 549/357, 377, 362, 366, 398, 399, 401; 546/152, 153; 544/49, 106, 349, 353

(56) References Cited

U.S. PATENT DOCUMENTS

| | | | |
|---|---|---|---|
| 5,648,368 A | 7/1997 | Egbertson et al. | 514/331 |
| 5,741,796 A | 4/1998 | Hartman et al. | 514/300 |

FOREIGN PATENT DOCUMENTS

| | | |
|---|---|---|
| DE | 19548709 | 7/1997 |
| DE | 19654483 | 1/1998 |
| WO | PCT9412181 | 6/1994 |
| WO | 9500536 | * 1/1995 |
| WO | PCT9532710 | 12/1995 |

OTHER PUBLICATIONS

Hoover et al, "A Quinoline N–Oxide analog of chloramphenicol", Chem. Abstr. CA 59:13946e, also cired as J. Med. Chem. 6/6,628–32(1963).*

Hagiwara etal;J.Med. Chem,"Studies in Neurokinin Antagonists.4 . . . ", 37/13,2090–9(1994).*

Darius H;"Oral GP llb/llla Antog. for Unstable Angina—"; Thrombosis Res. 103, 117–24(2001).*

* cited by examiner

Primary Examiner—Richard L. Raymond
Assistant Examiner—Subhaker R. Patel
(74) Attorney, Agent, or Firm—Millen, White, Zelano & Branigan, P.C.

(57) ABSTRACT

Compounds of the formula I

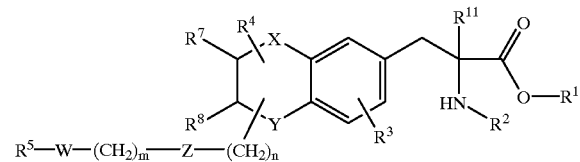

in which

X, Y, Z, $R^1$, $R^2$, $R^3$, $R^4$, $R^5$, $R^7$, $R^8$, $R^{11}$, m and n have the meanings stated in claim 1, and their physiologically acceptable salts can be used as integrin inhibitors, in particular for the prophylaxis and treatment of circulatory disorders, for thrombosis, myocardial infarct, coronary heart disease, arteriosclerosis, osteoporosis, for pathological processes maintained or propagated by angiogenesis, and in tumour therapy.

12 Claims, No Drawings

BICYCLIC AMINO ACIDS

This application is a division of application Ser. No. 09/367,219, filed Dec. 28, 1999, now ABN, which is a 371 of PCT/EP98/00636, filed Feb. 6, 1998.

The invention relates to compounds of the formula I

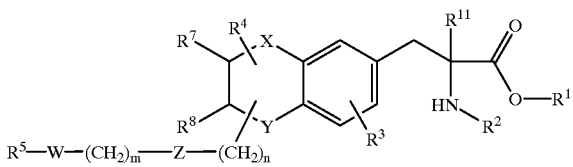

in which
R$^1$ is H, alkyl having 1–6 C atoms or benzyl,
R$^2$ is R$^{10}$, CO—R$^{10}$, COOR$^6$, COOR$^{10}$, SO$_2$R$^6$ or SO$_2$R$^{10}$,
R$^3$ is H, Hal, OA, NHR$^{10}$, N(R$^{10}$)$_2$, —NH-acyl, —O-acyl, CN, NO$_2$, OR$^{10}$, SR$^{10}$, R$^2$ or CONHR$^{10}$,
R$^4$ is H, =O, =S, C$_1$–C$_6$-alkyl or acyl,
R$^5$ is NH$_2$, H$_2$N—C(=NH) or H$_2$N—(C=NH)—NH, where the primary amino groups can also be provided with conventional amino protective groups or can be mono-, di- or trisubstituted by R$^{10}$, CO—R$^{10}$, COOR$^{10}$ or SO$_2$R$^{10}$, or R$^6$,
R$^7$, R$^8$ are each independently of one another absent or H,
R$^7$ and R$^8$ together are also a bond,
X, Y are each independently of one another =N—, —N—, O, S, —CH$_2$— or =C—, with the proviso that at least one of the two definitions X, Y is =N—, —N—, O or S,
W, z are each independently of one another absent, O, S, NR$^1$, C(=O), CONH, NHCO, C(=S)NH, NHC (=S), C(=S), SO$_2$NH, NHSO$_2$ or CA=CA',
R$^6$ is a mono- or binuclear heterocycle which has 1 to 4 N, O and/or S atoms and can be unsubstituted or mono-, di- or trisubstituted by Hal, A, —CO—A, OH, CN, COOH, COOA, CONH$_2$, NO$_2$, =NH or =O,
R$^9$ is H, Hal, OA, NHA, NAA', NHacyl, Oacyl, CN, NO$_2$, SA, SOA, SO$_2$A, SO$_2$Ar or SO$_3$H,
R$^{10}$ is H, A, Ar or aralkyl having 7–14 C atoms,
R$^{11}$ is H or alkyl having 1–6 C atoms,
A, A' are each independently of one another H or unsubstituted or mono-, di- or tri-R$^9$-substituted alkyl or cycloalkyl, each of which has 1–15 C atoms and in which one, two or three methylene groups can be replaced by N, O and/or S,
Ar is unsubstituted or mono-, di- or tri-A-and/or R$^9$-substituted mono- or binuclear aromatic ring system having 0, 1, 2, 3 or 4 N, O and/or S atoms,
Hal is F, Cl, Br or I and
m, n are each independently of one another 0, 1, 2, 3 or 4,
and the physiologically acceptable salts thereof.

Similar compounds are disclosed, for example, in WO 94/29273, WO 96/00730 and WO 96/18602.

The invention was based on the object of finding novel compounds with valuable properties, in particular those which can be used to produce pharmaceuticals.

It has been found that the compounds of the formula I and their salts have very valuable pharmacological properties while being well tolerated. In particular, they act as integrin inhibitors, inhibiting in particular the interactions of the α$_v$ integrin receptors with ligands. The compounds show particular activity in the case of the integrins α$_v$β$_3$ and α$_v$β$_5$. The compounds are very particularly active as adhesion receptor antagonists for the vitronectin receptor α$_v$β$_3$. This effect can be demonstrated, for example, by the method described by J. W. Smith et al. in J. Biol. Chem. 265, 11008–11013 and 12267–12271 (1990). B. Felding-Habermann and D. A. Cheresh describe, in Curr. Opin. Cell. Biol. 5, 864 (1993), the significances of the integrins as adhesion receptors for a wide variety of phenomena and pathological states, specifically relating to the vitronectin receptor α$_v$β$_3$.

The dependence of the initiation of angiogenesis on the interaction between vascular integrins and extracellular matrix proteins is described by P. C. Brooks, R. A. Clark and D. A. Cheresh in Science 264, 569–71 (1994).

The possibility of inhibiting this interaction and thus initiating apoptosis (programmed cell death) of angiogenic vascular cells by a cyclic peptide is described by P. C. Brooks, A. M. Montgomery, M. Rosenfeld, R. A. Reisfeld, T. Hu, G. Klier and D. A. Cheresh in Cell 79, 1157–64 (1994).

Experimental demonstration that the compounds according to the invention also prevent adhesion of living cells to the appropriate matrix proteins and, accordingly, also prevent the adhesion of tumour cells to matrix proteins can be provided by a cell adhesion assay carried out in analogy to the method of F. Mitjans et al., J. Cell Science 108, 2825–2838 (1995).

P. C. Brooks et al. describe, in J. Clin. Invest. 96, 1815–1822 (1995), α$_v$β$_3$ antagonists for controlling cancer and for treating tumour-induced angiogenic disorders. The compounds of the formula I according to the invention can therefore be employed as pharmaceutical agents, in particular for treating oncoses, osteoporoses and osteolytic disorders, and for suppressing angiogenesis.

Compounds of the formula I which block the interaction of integrin receptors and ligands such as, for example, of fibrinogen on the fibrinogen receptor (glycoprotein IIb/IIIa) prevent, as GPIIb/IIIa antagonists, the spread of tumour cells by metastasis. This is proved by the following observations: The spread of tumour cells from a local tumour into the vascular system takes place by formation of microaggregates (microthrombi) by the tumour cells interacting with blood platelets. The tumour cells are shielded by the protection in the microaggregate and are not recognized by the cells of the immune system. The microaggregates are able to become attached to vessel walls, facilitating further penetration of tumour cells into the tissue. Since the formation of microthrombi is mediated by fibrinogen binding to the fibrinogen receptors on activated blood platelets, the GPIIa/IIIb antagonists can be regarded as effective metastasis inhibitors.

Compounds of the formula I inhibit not only the binding of fibrinogen, fibronectin and Willebrand factor to the fibrinogen receptor of the blood platelets but also the binding of other adhesive proteins, such as vitronectin, collagen and laminin, to the corresponding receptors on the surface of various types of cells. They prevent, in particular, the development of blood platelet thrombi and can therefore be employed to treat thromboses, stroke, myocardial infarct, inflammations are arteriosclerosis.

The properties of the compounds can also be demonstrated by methods described in EP-A1 0 462 960. The inhibition of fibrinogen binding to the fibrinogen receptor can be demonstrated by the method indicated in EP-A1 0 381 033.

The platelet aggregation-inhibiting effect can be demonstrated in vitro by the method of Born (Nature 4832, 927–929, 1962).

The invention accordingly relates to compounds of the formula I according to claim 1 and/or their physiologically acceptable salts for producing a pharmaceutical for use as integrin inhibitors. The invention particularly relates to compounds of the formula I according to claim 1 and/or their acceptable salts in which $R^2$ is camphor-10-sulfonyl for producing a pharmaceutical for controlling pathologically angiogenic disorders, tumours, osteoporosis, inflammations and infections.

The compounds of the formula I can be employed as pharmaceutical agents in human and veterinary medicine, for the prophylaxis and/or therapy of thrombosis, myocardial infarct, arteriosclerosis, inflammations, stroke, angina pectoris, oncoses, osteolytic disorders such as osteoporosis, pathologically angiogenic disorders such as, for example, inflammations, ophthalmological disorders, diabetic retinopathy, macular degeneration, myopia, ocular histoplasmosis, rheumatoid arthritis, osteoarthritis, rubeotic glaucoma, ulcerative colitis, Crohn's disease, atherosclerosis, psoriasis, restenosis after angioplasty, viral infection, bacterial infection, fungal infection, in acute kidney failure and in wound healing to assist the healing processes.

The compounds of the formula I can be employed as substances with antimicrobial activity in operations where biomaterials, implants, catheters or heart pacemakers are used. They have an antiseptic effect in such cases. The efficacy of the antimicrobial activity can be demonstrated by the method described by P. Valentin-Weigund et al. in Infection and Immunity, 2851–2855 (1988).

The invention furthermore relates to a process for preparing compounds of the formula I according to claim 1 and salts thereof, characterized a) in that a compound of the formula I is liberated from one of its functional derivatives by treatment with a solvolysing or hydrogenolysing agent, or b) in that a compound of the formula II

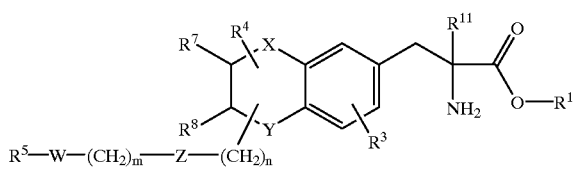

II in which $R^1$, $R^3$, $R^4$, $R^5$, $R^7$, $R^8$, $R^{11}$, W, X, Y, Z, m and n have the meanings stated in claim 1, is reacted with a compound of the formula III $R^2$—L III in which $R^2$ has the meaning stated in claim 1, and L is Cl, Br, I, OH or a reactively esterified OH group, or c) in that an ester of the formula I is hydrolysed, or d) in that a radical $R^1$ and/or $R^5$ is converted into another radical $R^1$ and/or $R^5$, and/or e) in that a basic or acidic compound of the formula I is converted by treatment with an acid or base into one of the salts thereof.

The compounds of the formula I have at least one chiral centre and may therefore occur in a plurality of stereoisomeric forms. All these forms (for example D and L forms) and mixtures thereof (for example the DL forms) are included in formula I. The compounds according to the invention also include so-called prodrug derivatives, that is to say compounds of the formula I which have been modified with, for example, alkyl or acyl groups, sugars or oligopeptides and which are rapidly cleaved in the body to give the active compounds according to the invention.

The abbreviations mentioned hereinbefore and hereinafter represent:

| | |
|---|---|
| Ac | acetyl |
| BOC | tert-butoxycarbonyl |
| CBZ or Z | benzyloxycarbonyl |
| DCCI | dicyclohexylcarbodiimide |
| DMF | dimethylformamide |
| DOPA | (3,4-dihydroxyphenyl)alanine |
| DPFN | 3,5-dimethylpyrazole-1-formamidinium nitrate |
| EDCI | N-ethyl-N'-(3-dimethylaminopropyl)carbodiimide |
| Et | ethyl |
| Fmoc | 9-fluorenylmethoxycarbonyl |
| HOBt | 1-hydroxybenzotriazole |
| Me | methyl |
| Mtr | 4-methoxy-2,3,6-trimethylphenylsulfonyl |
| HONSu | N-hydroxysuccinimide |
| OBn | benzyl ester |
| OBut | tert-butyl ester |
| Oct | octanoyl |
| OMe | methyl ester |
| OEt | ethyl ester |
| Orn | ornithine |
| POA | phenoxyacetyl |
| TBTU | O-(benzotriazol-1-yl)-N,N,N',N'-tetramethyluronium tetrafluoroborate |
| TFA | trifluoroacetic acid |
| Trt | trityl (triphenylmethyl) |
| Z or CBZ | benzyloxycarbonyl. |

All the radicals which occur more than once, such as, for example, A and A', can be identical or different, that is to say are independent of one another, and this applies to the entire invention.

In the formulae above, alkyl is preferably methyl, ethyl, propyl, isopropyl, butyl, isobutyl, sec-butyl or tert-butyl, also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2-, 1,2,2-trimethylpropyl, heptyl, octyl, nonyl or decyl.

Cycloalkyl is preferably cyclopropyl, cyclobutyl, cyclopentyl, cyclohexyl, cycloheptyl or 3-menthyl. Cycloalkyl is, in particular, the radical of a bicyclic terpene, and the camphor-10-yl radical is very particularly preferred.

Alkylene is preferably methylene, ethylene, propylene, butylene, pentylene, also hexylene, heptylene, octylene, nonylene or decylene. Aralkyl is preferably phenylalkyl and is, for example, preferably benzyl or phenethyl.

Cycloalkylene is preferably cyclopropylene, 1,2- or 1,3-cyclobutylene, 1,2- or 1,3-cyclopentylene, 1,2-, 1,3- or 1,4-cyclohexylene, also 1,2-, 1,3- or 1,4-cycloheptylene.

CO—A is alkanoyl or cycloalkanoyl and is preferably formyl, acetyl, propionyl, butyryl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl or octadecanoyl.

Acyl is $C_1$–$C_7$-acyl and has 1, 2, 3, 4, 5, 6 or 7 C atoms and is preferably, for example, formyl, acetyl, propionyl, butyryl, trifluoroacetyl or benzoyl.

Preferred substituents for alkyl, alkylene, cycloalkyl, cycloalkylene, alkanoyl and cycloalkanoyl are, for example, Hal, OA, NHA, NAA', CN, $NO_2$, SA, SOA, $SO_2A$, $SO_2Ar$ and/or $SO_3H$, in particular, for example, F, Cl, hydroxyl, methoxy, ethoxy, amino, dimethylamino, methylthio, methylsulfinyl, methylsulfonyl or phenylsulfonyl.

Preferred substituents for Ar and arylene are, for example, A and/or Hal, OA, NHA, NAA', CN, $NO_2$, SA, SOA, $SO_2A$, $SO_2Ar$ and/or $SO_3H$, in particular, for example, F, Cl, hydroxyl, methoxy, ethoxy, amino, dimethylamino, methylthio, methylsulfinyl, methylsulfonyl or phenylsulfonyl.

One, two or three methylene groups in each of the radicals alkyl, alkylene, cycloalkyl, cycloalkylene, alkanoyl and cycloalkanoyl can be replaced by N, O and/or S.

Ar—CO is aroyl and is preferably benzoyl or naphthoyl.

Ar is unsubstituted or preferably, as indicated, monosubstituted phenyl, specifically preferably phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-cyanophenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-methylthiophenyl, o-, m- or p-methylsulfinylphenyl, o-, m- or p-methylsulfonylphenyl, o-, m- or p-aminophenyl, o-, m- or p-methylaminophenyl, o-, m- or p-dimethylaminophenyl, o-, m- or p-nitrophenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl-4-chlorophenyl, 2-bromo-3-methyl-, 2-bromo-4-methyl-, 2-bromo-5-methyl-, 2-bromo-6-methyl-, 2-methyl-3-bromo-, 2-methyl-4-bromo-, 2-methyl-5-bromo-, 2-methyl-6-bromo-, 3-bromo-4-methyl, 3-bromo-5-methyl- or 3-methyl-4-bromophenyl, 2,4- or 2,5-dinitrophenyl, 2,5- or 3,4-dimethoxyphenyl, 2,3,4-, 2,3,5-, 2,3,6-, 2,4,6- or 3,4,5-trichlorphenyl, 2,4,6-tri-tert-butylphenyl, 2,5-dimethylphenyl, p-iodophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methylphenyl, 3-bromo-6-methoxyphenyl, 3-chloro-6-methoxyphenyl, 2-methoxy-5-methylphenyl, 2,4,6-triisopropylphenyl, naphthyl, 1,3-benzodioxol-5-yl, 1,4-benzodioxan-6-yl, benzothiadiazol-5-yl or benzoxadiazol-5-yl.

Ar is furthermore preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4-H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4- or 5-benzopyrazolyl, 2-, 4-, 5-, 6- or 7-benzoxazolyl, 3-, 4-, 5-, 6- or 7-benzisoxazolyl, 2-, 4-, 5-, 6- or 7-benzthiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl.

Arylene has the same meanings as indicated for Ar with the proviso that a further bond from the aromatic system is linked to the nearest bonding neighbour.

Heterocycloalkyl is preferably 1,2-, 2,3- or 1,3-pyrrolidinyl, 1,2-, 2,4-, 4,5- or 1,5-imidazolidinyl, 1,2-, 2,3- or 1,3-pyrazolidinyl, 2,3-, 3,4-, 4,5- or 2,5-oxazolidinyl, 1,2-, 2,3-, 3,4- or 1,4-isoxazolidinyl, 2,3-, 3,4-, 4,5- or 2,5-thiazolidinyl, 2,3-, 3,4-, 4,5- or 2,5-isothiazolidinyl, 1,2-, 2,3-, 3,4- or 1,4-piperidinyl, 1,4- or 1,2-piperazinyl, furthermore preferably 1,2,3-tetrahydrotriazol-1,2- or -1,4-yl, 1,2,4-tetrahydrotriazol-1,2- or 3,5-yl, 1,2- or 2,5-tetrahydrotetrazolyl, 1,2,3-tetrahydrooxadiazol-2,3-, -3,4-, -4,5- or -1,5-yl, 1,2,4-tetrahydro-oxadiazol-2,3-, -3,4- or -4,5-yl, 1,3,4-tetrahydro-thiadiazol-2,3-, -3,4-, -4,5- or -1,5-yl, 1,2,4-tetrahydrothiadiazol-2,3-, -3,4-, -4,5- or -1,5-yl, 1,2,3-thiadiazol-2,3-, -3,4-, -4,5- or -1,5-yl, 2,3- or 3,4-morpholinyl, 2,3-, 3,4- or 2,4-thiomorpholinyl.

$R^6$ is a mono- or binuclear heterocycle, preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4-H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzthiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl.

The heterocyclic radicals can also be partly or completely hydrogenated.

$R^6$ can thus also be, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl.

The said heterocyclic radicals may also be substituted once, twice or three times by Hal, A, —CO— A, OH, CN, COOH, COOA, $CONH_2$, $NO_2$, =NH or =O.

$R^6$ is very particularly 1H-imidazol-2-yl, thiazol-2-yl, 1H-benzimidazol-2-yl, 2H-pyrazol-2-yl, 1H-tetrazol-5-yl, 2-iminoimidazolidin-4-on-5-yl, 1-alkyl-1,5-dihydroimidazol-4-on-2-yl, pyrimidin-2-yl or 1,4,5,6-tetrahydropyrimidin-2-yl.

$R^{11}$ is H or alkyl with 1–6 C atoms, preferably H.

Accordingly the invention particularly relates to those compounds of the formula I in which at least one of the said radicals has one of the preferred meanings stated above. Some preferred groups of compounds can be represented by the following part-formulae Ia to Ig which correspond to the formula I and in which the undefined radicals have the meanings stated for formula I, but in which in Ia)

| Ia) | $R^1$ | is H or alkyl with 1–6 C atoms, |
| --- | --- | --- |
| | $R^2$ | is $R^{10}$, CO—$R^{10}$, COO$R^{10}$ or SO$_2R^{10}$, |
| | $R^3$ | is H, |
| | $R^4$ | is H or =O, |
| | $R^5$ | is H$_2$N—C(=NH) or H$_2$N—C(=NH)—NH, |
| | W, Z | are each independently of one another absent, C(=O), NH, CONH or NHCO, |
| | X | is —NH—, O or —CH$_2$—, |
| | Y | is NH or O, |
| | $R^{10}$ | is H, A or benzyl, |
| | $R^{11}$ | is H, |
| | A | is unsubstituted alkyl or cycloalkyl with 1–15 C atoms and |
| | m, n | are each independently of one another 0, 1 or 2; | in Ib)

| Ib) | $R^1$ | is H or alkyl with 1–6 C atoms, |
| --- | --- | --- |
| | $R^2$ | is $R^{10}$, CO—$R^{10}$, COO$R^{10}$ or SO$_2R^{10}$, |
| | $R^3$ | is H, |
| | $R^4$ | is H or =O, |
| | $R^5$ | is $R^6$, |
| | W, Z | are each independently of one another absent, C(=O), NH, CONH or NHCO, |
| | X | is —NH—, O or —CH$_2$—, |
| | Y | is NH or O, |
| | $R^6$ | is a mono- or binuclear heterocycle which has 1–4 N, O and/or S atoms and which can be unsubstituted or mono-, di- or trisubstituted by Hal, A, —CO—A, OH, CN, COOH, COOA, CONH$_2$, NO$_2$, =NH or =O, |
| | $R^{10}$ | is H, A or benzyl, |
| | $R^{11}$ | is H, |
| | A | is unsubstituted alkyl or cycloalkyl with 1–15 C atoms and |
| | m, n | are each independently of one another 0, 1 or 2; | in Ic)

| Ic) | $R^1$ | is H or alkyl with 1–6 C atoms, |
| --- | --- | --- |
| | $R^2$ | is $R^{10}$, CO—$R^{10}$, COO$R^{10}$ or SO$_2R^{10}$, |
| | $R^3$ | is H, |
| | $R^4$ | is H or =O, |
| | $R^5$ | is H$_2$N—C(=NH) or H$_2$N—C(=NH)—NH, |
| | W, Z | are each independently of one another absent, C(=O), NH, CONH or NHCO, |
| | X | is —NH—, O or —CH$_2$—, |
| | Y | is NH or O, |
| | A | is alkyl with 1–6 C atoms, |
| | $R^{10}$ | is H, alkyl with 1–6 C atoms, camphor-10-yl or benzyl, |
| | $R^{11}$ | is H, |
| | m, n | are each independently of one another 0, 1 or 2; | in Id)

| Id) | $R^1$ | is H or alkyl with 1–6 C atoms, |
| --- | --- | --- |
| | $R^2$ | is $R^{10}$, CO—$R^{10}$, COO$R^{10}$ or SO$_2R^{10}$, |
| | $R^3$ | is H, |
| | $R^4$ | is H or =O, |
| | $R^5$ | is $R^6$, |
| | W, Z | are each independently of one another absent, C(=O), NH, CONH or NHCO, |
| | X | is =NH—, O or —CH$_2$—, |
| | Y | is NH or O, |
| | $R^6$ | is a mono- or binuclear heterocycle which has 1–4 N, O and/or S atoms and which can be unsubstituted or mono-, di- or trisubstituted by Hal, A, —CO—A, OH, CN, COOH, COOA, CONH$_2$, NO$_2$, =NH or =O, |
| | $R^{10}$ | is H, alkyl with 1–4 C atoms, camphor-10-yl or benzyl, |
| | $R^{11}$ | is H, |
| | A | is unsubstituted alkyl with 1–6 C atoms and |
| | m, n | are each independently of one another 0, 1 or 2; | in Ie)

| Ie) | $R^1$ | is H or alkyl with 1–6 C atoms, |
| --- | --- | --- |
| | $R^2$ | is $R^{10}$, CO—$R^{10}$, COO$R^{10}$ or SO$_2R^{10}$, |
| | $R^3$ | is H, |
| | $R^4$ | is H or =O, |
| | $R^5$ | is $R^6$, |
| | W, Z | are each independently of one another absent, C(=O), NH, CONH or NHCO, |
| | X | is —NH—, O or —CH$_2$—, |
| | Y | is NH or O, |
| | $R^6$ | is 1H-imidazol-2-yl, thiazol-2-yl, 1H-benzimidazol-2-yl, 2H-pyrazol-2-yl, 1H-tetrazol-5-yl, 2-imino-imidazolidin-4-on-5-yl, 1-A-1, 5-dihydro-imidazol-4-on-2-yl, pyrimidin-2-yl or 1,4,5,6-tetrahydro-pyrimidin-yl, |
| | $R^{10}$ | is H, alkyl with 1–4 C atoms, camphor-10-yl or benzyl, |
| | $R^{11}$ | is H, |
| | A | is unsubstituted alkyl with 1–6 C atoms and |
| | m, n | are each independently of one another 0, 1 or 2; | in If)

| If) | $R^1$ | is H or alkyl with 1–6 C atoms, |
| --- | --- | --- |
| | $R^2$ | is $R^{10}$, CO—$R^{10}$, COO$R^{10}$ or SO$_2R^{10}$, |
| | $R^3$ | is H, |
| | $R^4$ | is H or =O, |
| | $R^5$ | is H$_2$N—C(=NH) or H$_2$N—C(=NH)—NH, |
| | W, Z | are each independently of one another absent, C(=O), NH, CONH or NHCO, |
| | X | is —NH—, O or —CH$_2$—, |
| | Y | is NH or O, |
| | $R^{10}$ | is Ar, |
| | $R^{11}$ | is H, |
| | A | is unsubstituted alkyl or cycloalkyl with 1–15 C atoms and |
| | m, n | are each independently of one another 0, 1 or 2; | in Ig)

| Ig) | $R^1$ | is H or alkyl with 1–6 C atoms, |
| --- | --- | --- |
| | $R^2$ | is $R^{10}$, CO—$R^{10}$, COO$R^{10}$ or SO$_2R^{10}$, |

-continued

| | |
|---|---|
| $R^3$ | is H, |
| $R^4$ | is H or =O, |
| $R^5$ | $R^6$, |
| W, Z | are each independently of one another absent, C(=O), NH, CONH or NHCO, |
| X | is —NH—, O or —CH$_2$—, |
| Y | is NH or O, |
| $R^6$ | is a mono- or binuclear heterocycle which has 1–4 N, O and/or S atoms and which can be unsubstituted or mono-, di- or trisubstituted by Hal, A, —CO—A, OH, CN, COOH, COOA, CONH$_2$, NO$_2$, =NH or =O, |
| $R^{10}$ | is Ar, |
| $R^{11}$ | is H, |
| A | is unsubstituted alkyl or cycloalkyl with 1–15 C atoms and |
| m, n | are each independently of one another 0, 1 or 2. |

The compounds of the formula I and the starting materials for preparing them are moreover prepared by methods known per se, as described in the literature (for example in the stardard works such as Houben-Weyl, Methoden der organischen Chemie [Methods of Organic Chemistry], Georg-Thieme-Verlag, Stuttgart), specifically under reaction conditions known and suitable for the said reactions. It is also possible for this purpose to make use of variants which are known per se but which are no mentioned in detail here.

The starting materials can, if required, also be formed in situ so that they are not isolated from the reaction mixture but immediately reacted further to give the compounds of the formula I.

Compounds of the formula I can preferably be obtained by liberating compounds of the formula I from one of the functional derivatives thereof by treatment with a solvolysing or hydrogenolysing agent.

Preferred starting materials for the solvolysis or hydrogenolysis are those which otherwise correspond to the formula I but comprise in place of one or more free amino and/or hydroxyl groups corresponding protected amino and/or hydroxyl groups, preferably those which have an amino protective group in place of an H atom bonded to an N atom, especially those which have an R'—N group in place of an HN group, in which R' is an amino protective group, and/or those which have a hydroxyl protective group in place of the H atom of a hydroxyl group, for example those which correspond to the formula I but have a group —COOR" in place of a group —COOH, in which R" is a hydroxyl protective group.

It is also possible for a plurality of identical or different protected amino and/or hydroxyl groups to be present in the molecule of the starting material. If the protective groups present are different from one another, they can in many cases be eliminated selectively.

The term "amino protective group" is generally known and refers to groups which are suitable for protecting (blocking) an amino group from chemical reactions but which can easily be removed after the required chemical reaction elsewhere in the molecule has been carried out. Typical groups of this type are, in particular, unsubstituted or substituted acyl, aryl, aralkoxymethyl or aralkyl groups. Since the amino protective groups are removed after the required reaction (or sequence of reactions), their nature and size are not otherwise critical; however, those with 1–20, in particular 1–8, C atoms are preferred. The term "acyl group" is to be interpreted in the widest sense in connection with the present process. It embraces acyl groups derived from aliphatic, araliphatic, aromatic or heterocyclic carboxylic acids or sulfonic acids and, in particular, alkoxycarbonyl, aryloxycarbonyl and, especially, aralkoxycarbonyl groups. Examples of such acyl groups are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC, 2-iodoethoxycarbonyl; aralkyloxycarbonyl such as CBZ ("carbobenzoxy"), 4-methoxybenzyloxycarbonyl, FMOC; arylsulfonyl such as Mtr. Preferred amino protective groups are BOC and Mtr, also CBZ, FMOC, benzyl and acetyl.

The amino protective group is eliminated, depending on the protective group used, for example with strong acids, preferably with TFA or perchloric acid, but also with other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible but not always necessary. Suitable and preferred inert solvents are organic, for example carboxylic acids such as acetic acid, ethers such as tetrahydrofuran or dioxane, amides such as DMF, halogenated hydrocarbons such as dichloromethane, also alcohols such as methanol, ethanol or isopropanol, and water. Mixtures of the abovementioned solvents are also suitable. TFA is preferably used in excess without addition of another solvent, and perchloric acid is used in the form of a mixture of acetic acid and 70% perchloric acid in the ratio 9:1. The reaction temperatures for the cleavage are preferably between about 0 and about 50°, preferably between 15 and 30° (room temperature).

The BOC, OBut and Mtr groups can be eliminated, for example, preferably with TFA in dichloromethane or with approximately 3 to 5N HCl in dioxane at 15–30°, and the FMOC group can be eliminated with an approximately 5 to 50% solution of dimethylamine, diethylamine or piperidine in DMF at 15–30°.

Protective groups which can be removed by hydrogenolysis (for example CBZ or benzyl) can be eliminated, for example, by treatment with hydrogen in the presence of a catalyst (for example of a noble metal catalyst such as palladium, preferably on a support such as carbon). Suitable solvents in this case are those indicated above, in particular, for example, alcohols such as methanol or ethanol or amides such as DMF. The hydrogenolysis is, as a rule, carried out at temperatures between about 0 and 100° under pressures between about 1 and 200 bar, preferably at 20–30° under 1–10 bar. Hydrogenolysis of the CBZ group takes place satisfactorily, for example, on 5 to 10% Pd/C in methanol or with ammonium formate (in place of hydrogen) on Pd/C in methanol/DMF at 20–30°.

Compounds of the formula I can preferably be obtained by reacting compounds of the formula II with compounds of the formula III. The starting compounds of the formula II and III are, as a rule, novel. However, they can be prepared by methods known per se.

In the compounds of the formula III, L is preferably Cl, Br, I or a reactively modified OH group such as alkylsulfonyloxy with 1–6 C atoms (preferably methylsulfonyloxy) or arylsulfonyloxy with 6–10 C atoms (preferably phenyl- or p-tolylsulfonyloxy).

The compounds of the formula II are, as a rule, reacted in an inert solvent in the presence of an acid-binding agent, preferably of an organic base such as triethylamine, dimethylaniline, pyridine or quinoline. It may also be beneficial to add an alkali metal or alkaline earth metal hydroxide, carbonate or bicarbonate or another salt of a weak acid of the alkali metals or alkaline earth metals, preferably of potassium, sodium, calcium or caesium.

The reaction time depends on the conditions applied and is between a few minutes and 14 days, and the reaction temperature is between about −30° and 140°, normally between −10° and 90°, in particular between about 0° and about 70°.

Examples of suitable inert solvents are hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methylglycol or ethylglycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate, water or mixtures of the solvents mentioned.

It is furthermore possible to hydrolyse an ester of the formula I. This is preferably carried out by solvolysis or hydrogenolysis as indicated above, for example with NaOH or KOH in dioxane/water at temperatures between 0 and 60° C., preferably between 10 and 40° C.

It is furthermore possible to convert a radical $R^1$ and/or $R^5$ into another radical $R^1$ and/or $R^5$. In particular, it is possible to convert a carboxylic acid into a carboxylic ester.

A cyano group is converted into an amidino group by reaction with, for example, hydroxylamine and subsequent reduction of the N-hydroxyamidine with hydrogen in the presence of a catalyst such as, for example, Pd/C.

It is furthermore possible to replace a conventional amino protective group by hydrogen by eliminating the protective group by solvolysis or hydrogenolysis as described above, or by liberating an amino group protected by a conventional protective group by solvolysis or hydrogenolysis.

A base of the formula I can be converted with an acid into the relevant acid addition salt, for example by reacting equivalent amounts of the base and of the acid in an inert solvent such as ethanol and subsequently evaporating. Acids particularly suitable for this reaction are those which provide physiologically acceptable salts. Thus, it is possible to use inorganic acids, for example sulfuric acid, nitric acid, hydrohalic acids such as hydrochloric acid or hydrobromic acid, phosphoric acids such as orthophosphoric acid, sulfamic acid, also organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, lauryl sulfuric acid. Salts with physiologically unacceptable acids, for example picrates, can be used for isolating and/or purifying the compounds of the formula I.

On the other hand, an acid of the formula I can be converted by reaction with a base into one of its physiologically acceptable metal or ammonium salts. Suitable salts in this connection are, in particular, the sodium, potassium, magnesium, calcium and ammonium salts, also substituted ammonium salts, for example the dimethyl-, diethyl- or diisopropylammonium salts, monoethanol-, diethanol- or diisopropanolammonium salts, cyclohexyl, dicyclohexylammonium salts, dibenzylethylenediammonium salts, furthermore, for example, salts with arginine or lysine.

The compounds of the formula I contain one or more chiral centres and may therefore exist in racemic or in optically active form. Resulting racemates can be resolved mechanically or chemically by methods known per se into the enantiomers. Preferably, diastereomers are formed from the racemic mixture by reaction with an optically active resolving agent. Examples of suitable resolving agents are optically active acids such as the D and L forms of tartaric acid, diacetyltartaric acid, dibenzoyltartaric acid, mandelic acid, malic acid, lactic acid or the various optically active camphorsulfonic acids such as β-camphorsulfonic acid. An advantageous enantiomer resolution also makes use of a column packed with an optically active resolving agent (for example dinitrobenzoylphenylglycine); an example of a suitable mobile phase is a hexane/isopropanol/acetonitrile mixture, for example in the ratio 82:15:3 by volume.

It is, of course, also possible to obtain optically active compounds of the formula I by the methods described above by using starting materials which are already optically active.

The invention furthermore relates to the use of the compounds of the formula I and/or the physiologically acceptable salts thereof for producing pharmaceutical compositions, in particular by non-chemical means. For this purpose they can be converted together with at least one solid, liquid and/or semiliquid excipient or ancillary substance and, where appropriate, in combination with one or more other active ingredients into a suitable dosage form.

The invention furthermore relates to pharmaceutical compositions comprising at least one compound of the formula I and/or one of the physiologically acceptable salts thereof.

These compositions can be used as pharmaceuticals in human or veterinary medicine. Suitable excipients are organic or inorganic substances which are suitable for enteral (for example oral), parenteral, topical administration or for administration in the form of an inhalation spray and which do not react with the novel compounds, for example water, vegetable oils, benzyl alcohols, alkylene glycols, polyethylene glycols, glycerol triacetate, gelatin, carbohydrates such as lactose or starch, magnesium stearate, talc, petrolatum. Used for oral administration are, in particular, tablets, pills, coated tablets, capsules, powders, granules, syrups, solutions or drops, for rectal administration are suppositories, for parenteral administration are solutions, preferably oily or aqueous solutions, also suspensions, emulsions or implants, and for topical administration are ointments, creams or dusting powders. The novel compounds can also be lyophilized, and the resulting lyophilisates can be used, for example, for producing products for injection. The stated compositions can be sterilized and/or comprise ancillary substances such as lubricants, preservatives, stabilizers and/or wetting agents, emulsifiers, salts to influence the osmotic pressure, buffer substances, colourants, flavourings and/or several other active ingredients, for example one or more vitamins. The sprays which can be used for administration as inhalation spray comprise the active ingredient either dissolved or suspended in a propellant gas or mixture of propellant gases (for example $CO_2$ or chlorofluoro-carbons). In this case, the active ingredient is preferably used in micronized form, and it is possible for one or more additional physiologically tolerated solvents to be present, for example ethanol. Solutions for inhalation can be administered using conventional inhalers.

The compounds of the formula I and their physiologically acceptable salts can be used as integrin inhibitors for controlling diseases, in particular pathologically angiogenic disorders, thromboses, myocardial infarct, coronary heart disease, arteriosclerosis, tumours, inflammations and infections.

Compounds of the formula I according to claim 1 and/or their acceptable salts in which $R^2$ is camphor-10-yl are preferred for controlling pathologically angiogenic disorders, tumours, osteoporosis, inflammations and infections.

In this connection it is possible for the substances according to the invention to be administered, as a rule, in analogy to other known and commercially available peptides, but especially in analogy to the compounds described in U.S. Pat. No. 4,472,305, preferably in dosages between about 0.05 and 500 mg, in particular between 0.5 and 100 mg per dosage unit. The daily dose is preferably between about 0.01 and 2 mg/kg of body weight. The specific dose for each patient depends, however, on a wide variety of factors, for example on the activity of the specific compound employed, on the age, body weight, general state of health, sex, on the diet, on the time and route of administration, on the rate of excretion, combination of medicinal substances and severity of the particular disorder for which the therapy is applied. Parenteral administration is preferred.

All temperatures hereinbefore and hereinafter are stated in ° C. In the following examples, "usual workup" means: if necessary, water is added, if necessary, depending on the constitution of the final product, the pH is adjusted to between 2 and 10, extraction is carried out with ethyl acetate or dichloromethane, and the organic phase is separated off, dried over sodium sulfate, evaporated and purified by chromatography on silica gel and/or by crystallization.

Mass spectrometry (MS): EI (electron impact ionization) M+

FAB (fast atom bombardment) (M+H)+

EXAMPLE 1

A solution of 12 g of BOC-3-nitro-L-tyrosine benzyl ester ("1") in 200 ml of THF is hydrogenated in the presence of 1 g of Raney nickel at room temperature under atmospheric pressure for 6 hours. The catalyst is removed, and the usual workup results in 11.7 g of BOC-3-amino-L-tyrosine benzyl ester ("2"), FAB 387.

A solution of 9.3 g of "2", 2.36 g of maleic anhydride and 3.3 ml of triethylamine in 150 ml of DMF is heated to 80° and then stirred for 12 hours. The solvent is removed and the residue is chromatographed on silica gel with dichloromethane/methanol 20:1–10:1 as eluent. 5.1 g of benzyl (2S)-2-tert-butyloxycarboxamido-3-(3,4-dihydro-2-carboxymethyl-2H-1,4-benzoxazin-3-on-6-yl)-propionate are obtained as diastereomer mixture ("3") FAB 485.

1 g of Z-guanidine and 1.75 ml of ethyldiiso-propylamine are added to a solution of 1 g of "3" and 0.79 g of 2-chloro-1-methylpyridinium iodide in 20 ml of DMF, and the mixture is stirred at room temperature for 12 hours. The usual workup results after chromatography on silica gel (toluene/methanol 10:1) in 0.2 g of benzyl (2S)-2-tert-butyloxycarboxamido-3-[3,4-dihydro-2-(2-benzyloxycarbonylguanidino-2-oxoethyl)-2H-1,4-benzoxazin-3-on-6-yl]propionate ("4"), FAB 660.

A solution of 200 mg of "4" and 3 ml of water/3 ml of dioxane is hydrogenated in the presence of 100 mg of palladium (10% on active carbon) at RT under atmospheric pressure. The pH is kept at 4–5 by adding 1N HCl. The catalyst and the solvent are removed. The residue is purified by preparative HPLC (RP-18 with acetonitrile/water+0.3% TFA gradient from 1:80 to 99:1 in one hour) to result in 40 mg of (2S)-2-tert-butyloxycarboxamido-3-[3,4-dihydro-2-(2-guanidino-2-oxoethyl)-2H-1,4-benzoxazin-3-on-6-yl] pro-pionic acid ("5"), trifluoroacetate, FAB 660.

EXAMPLE 2

2.3 g of potassium carbonate are added to a solution of 6 g of Z-L-DOPA ethyl ester ("6") in 25 ml of ethanol and 25 ml of water under protective gas. The mixture is heated to 60°, 4.5 ml of epibromohydrin are added, and the mixture is heated to 90°. After stirring for 2 hours and the usual workup, the crude product is purified on silica gel. 5.6 g of a mixture ("8") of the diastereomeric pairs of positional isomers, which cannot be separated, are obtained: ethyl (2S)-2-benzyloxycarboxamido-3-(3-(3R,3S)-hydroxymethyl-1,4-benzodioxan-6-yl)propionate ("7a") and ethyl (2S)-2-benzyloxycarboxamido-3-(2-(2R,2S)-hydroxymethyl-1,4-benzodioxan-6-yl)propionate ("7b"), FAB 416.

0.413 ml of methanesulfonyl chloride is added to a solution of 2 g of "8" in 30 ml of pyridine at 0° and, after stirring for 2 hours, the usual workup is carried out. 2.2 g of ethyl (2S)-2-benzyloxycarbox-amido-3-(⅔-methylsulfonyloxymethyl-1,4-benzodioxan-6-yl)propionate ("9") are obtained, FAB 494.

A solution of 1.6 g of "9", 1.6 g of sodium azide and 30 ml of DMF is stirred at 75° for 12 hours. The usual workup results in ethyl (2S)-2-benzyl-oxycarboxamido-3-(⅔-azidomethyl-1,4-benzodioxan-6-yl) propionate ("10"), FAB 441.

3.4 ml of 1N sodium hydroxide solution are added to a solution of 1.25 g of "10" and 25 ml of methanol and stirred at room temperature for 12 hours. The usual workup results in 1.3 g of (2S)-2-benzyloxy-carboxamido-3-(⅔-azidomethyl-1,4-benzodioxan-6-yl)-propionic acid ("11"), FAB 413.

Hydrogen sulfide is passed into a solution of 1.3 g of "11" in 40 ml of pyridine and 20 ml of water at room temperature for 30 min, and it is then left to stand for 12 hours. Removal of the solvent results in 1.5 g of (2S)-2-benzyloxycarboxamido-3-(⅔-amino-methyl-1,4-benzodioxan-6-yl)propionic acid ("12"), FAB 387.

A solution of 0.3 g of "12", 0.23 g of 3,5-dimethylpyrazole-1-formamidinium nitrate (DPFN) and 0.22 ml of triethylamine in 10 ml of DMF is stirred at 60° for 12 hours. The usual workup with preparative HPLC (conditions analogous to Example 1 for purifying "5") results in separation of the 2-guanidinomethyl compounds from the 3-guanidinomethyl compounds.

Yield: 80 mg of (2S)-2-benzyloxycarboxamido-3-(2-(2R, S)-guanidinomethyl-1,4-benzodioxan-6-yl)propionic acid ("13"), FAB 429.

EXAMPLE 3

A solution of 0.95 g of BOC-glycine and 0.96 g of carbonyldiimidazole in 20 ml of THF is stirred for 2 hours. Then 0.7 g of "12" is added and the mixture is stirred for 12 hours. The usual workup results in 0.66 g of (2S)-2-benzyloxycarboxamido-3-(⅔-tert-butyloxycarboxamidoacetamidomethyl-1,4-benzodioxan-6-yl)-propionic acid ("14"), FAB 544.

0.5 ml of trifluoroacetic acid is added to a solution of 0.15 g of "14" in 5 ml of dichloromethane and stirred for 8 hours.

After removal of the solvent, 10 ml of DMF are added, followed by 80 mg of DPFN and 70 μl of triethylamine. The mixture is heated to 80° and stirred for 12 hours. Purification and fractionation of the ⅔ isomers take place by preparative HPLC in analogy to Example 1.

42 mg of (2S)-2-benzyloxycarboxamido-3-(2-guanidino-acetamidomethyl-1,4-benzodioxan-6-yl)propionic acid ("15") are obtained, FAB 486.

EXAMPLE 4

Hydrogen is passed for 2 hours through a solution of 0.45 g of "14" in 10 ml of dioxane and 5 ml of water in the presence of 0.2 g of palladium (10% on active carbon). Removal of the catalyst and the usual workup result in 0.28 g of (2S)-2-amino-3-(⅔-tert-butyloxycarboxamidoacetamidomethyl-1,4-benzodioxan-6-yl)propionic acid ("16"), FAB 410.

430 μl of N,O-bis(trimethylsilyl)trifluoroacetamide (BSTFA) are added to a solution of 0.28 g of "16" in 5 ml of acetonitrile, and the mixture is then boiled under reflux for 3 hours. Then 66 μl of pyridine and 0.188 g of R-camphor-10-sulfonyl chloride are added, and the mixture is stirred at 70° for 3 hours. The usual workup results in 0.26 g of (2S)-2-(R)-camphorsulfonamido-3-(⅔-tert-butyloxycarboxamido-acetamidomethyl-1,4-benzodioxan-6-yl)propionic acid ("17"), FAB 624.

Elimination of the BOC group from 0.25 g of "17" and guanylation in analogy to the preparation of "15" result in 58 mg of (2S)-2-(R)-camphorsulfonamido-3-(2-guanidinoacetamidomethyl-1,4-benzodioxan-6-yl)propicnic acid ("18"), FAB 566.

Analogous reaction of "16" with butylsulfonyl chloride results in (2S)-2-butylsulfonamido-3-(⅔-tert-butyloxycarboxamidoacetamidomethyl-1,4-benzodioxan-6-yl)propionic acid;

with 4-tolylsulfonyl chloride results in (2S)-2-(4-tolylsulfonamido)-3-(⅔-tert-butyloxycarboxamidoacetamidomethyl-1,4-benzodioxan-6-yl)-propionic acid;

with benzylsulfonyl chloride results in (2S)-2-benzylsulfonamido-3-(⅔-tert-butyloxycarboxamidoacetamidomethyl-1,4-benzodioxan-6-yl)propionic acid;

with phenylsulfonyl chloride results in (2S)-2-phenylsulfonamido-3-(⅔-tert-butyloxycarboxamidoacetamidomethyl-1,4-benzodioxan-6-yl)propionic acid;

with 2-naphthylsulfonyl chloride results in (2S)-2-(2-naphthylsulfonamido)-3-(⅔-tert-butyloxycarboxamidoacetamidomethyl-1,4-benzodioxan-6-yl)-propionic acid and with cyclohexylsulfonyl chloride results in (2S)-2-cyclohexylsulfonamido-3-(⅔-tert-butyloxycarboxamidoacetamidomethyl-1,4-benzodioxan-6-yl)-propionic acid.

Elimination of the BOC croup therefrom and guanylation result in (2S)-2-butylsulfonamido-3-(2-guanidinoacetamidomethyl-1,4-benzodioxan-6-yl) propionic acid;

(2S)-2-(4-tolylsulfonamido-3-(2-guanidinoacetamidomethyl-1,4-benzodioxan-6-yl) propionic acid;

(2S)-2-benzylsulfonamido-3-(2-guanidinoacetamidomethyl-1,4-benzodioxan-6-yl) propionic acid;

(2S)-2-phenylsulfonamido-3-(2-guanidinoacetamidomethyl-1,4-benzodioxan-6-yl) propionic acid;

(2S)-2-(2-naphthylsulfonamido)-3-(2-guanidinoacetamidomethyl-1,4-benzodioxan-6-yl) propionic acid and (2S)-2-cyclohexylsulfonamido-3-(2-guanidinoacetamidomethyl-1,4-benzodioxan-6-yl) propionic acid.

EXAMPLE 5

0.26 g of TBTU, 26 mg of HOBT and 0.34 ml of N-methylmorpholine are added to a solution of 0.3 g of "3" and 0.248 g of 2-aminobenzimidazole ("A") in 10 ml of DMF and stirred at room temperature for 12 hours. The usual workup results in 0.14 g of benzyl (2S)-2-tert-butyloxycarboxamido-3-{3,4-dihydro-2-[N-(2-benzimidazolyl)carbamoylmethyl]-2H-1,4-benzoxazin-3-on-6-yl)-propionate ("19").

Hydrogenation of "19" in analogy to Example 1 results in 60 mg of (2S)-2-tert-butyloxycarboxamido-3-{3,4-dihydro-2-[N-(2-benzimidazolyl)carbamoylmethyl]-2H-1,4-benzoxazin-3-on-6-yl}propionic acid ("122"), FAB 510.

Analogous reaction of "3"
with 2-aminoimidazole ("B") results in benzyl (2S)-2-tert-butyloxycarboxamido-3-{3,4-dihydro-2-[N-(2-imidazolyl)carbamoylmethyl]-2H-1,4-benzoxazin-3-on-6-yl}propionate ("20")

and subsequent cleavage of the benzyl ester results in (2S)-2-tert-butyloxycarboxamido-3-{3,4-dihydro-2-[N-(2-imidazolyl)carbamoylmethyl]-2H-1,4-benzoxazin-3-on-6-yl}propionic acid ("23"), FAB 460;

and with 2-aminomethylbenzimidazole ("C") results in benzyl (2S)-2-tert-butyloxycarboxamido-3-{3,4-dihydro-2-[N-(2-benzimidazolylmethyl)carbamoylmethyl]-2H-1,4-benzoxazin-3-on-6-yl}propionate ("21"), and subsequent cleavage of the benzyl ester results in (2S)-2-tert-butyloxycarboxamido-3-{3,4-dihydro-2-[N-(2-benzimidazolylmethyl)carbamoylmethyl]-2H-1,4-benzoxazin-3-on-6-yl}propionic acid ("24"), FAB 524.

EXAMPLE 6

5 ml of TFA are added to a solution of 2 g of "3" in 50 ml of dichloromethane and stirred at room temperature for 1 hour. Removal of the solvent results in 2 g of benzyl (2S)-amino-3-(3,4-dihydro-2-carboxymethyl-2H-1,4-benzoxazin-3-on-6-yl)propionate, trifluoroacetate ("25"), FAB 385.

1.2 ml of BSTFA are added to a solution of 1 g of "25" and 0.3 ml of triethylamine in 25 ml of acetonitrile and then boiled under reflux for 2 hours. Then, at 40°, 0.19 ml of pyridine and 0.55 g of (R)-camphor-10-sulfonyl chloride are added, and stirred at 70° for 12 hours. The usual workup results in 0.41 g of benzyl (2S)-2-[(R)-camphorsulfonamido]-3-(3,4-dihydro-2-carboxymethyl-2H-1,4-benzoxazin-3-on-6-yl)propionate ("26"), FAB 599.

Analogous reaction of "25"
with butylsulfonyl chloride results in benzyl (2S)-2-butylsulfonamido-3-(3,4-dihydro-2-carboxymethyl-2H-1,4-benzoxazin-3-on-6-yl)propionate;

with 4-tolylsulfonyl chloride results in benzyl (2S)-2-(4-tolylsulfonamido)-3-(3,4-dihydro-2-carboxymethyl-2H-1,4-benzoxazin-3-on-6-yl)propionate;

with benzylsulfonyl chloride results in benzyl (2S)-2-benzylsulfonamido-3-(3,4-dihydro-2-carboxymethyl-2H-1,4-benzoxazin-3-on-6-yl)propionate;

with phenylsulfonyl chloride results in
  benzyl (2S)-2-phenylsulfonamido-3-(3,4-dihydro-2-carboxymethyl-2H-1,4-benzoxazin-3-on-6-yl)propionate;
  with 2-naphthylsulfonyl chloride results in benzyl (2S)-2-(2-naphthylsulfonamido)-3-(3,4-dihydro-2-carboxymethyl-2H-1,4-benzoxazin-3-on-6-yl)propionate
and with cyclohexylsulfonyl chloride results in
  benzyl (2S)-2-cyclohexylsulfonamido-3-(3,4-dihydro-2-carboxymethyl-2H-1,4-benzoxazin-3-on-6-yl)-propionate
  Reaction of "26" in analogy to Example 5
  with "A" results in benzyl (2S)-2-[(R)-camphorsulfonamido]-3-{3,4-dihydro-2-[N-(2-benzimidazolyl)carbamoylmethyl]-2H-1,4-benzoxazin-3-on-6-yl)propionate ("27"), FAB 714,
with "B" results in
  benzyl (2S)-2-[(R)-camphorsulfonamido]-3-{3,4-dihydro-2-[N-(2-imidazolyl)carbamoylmethyl]-2H-1,4-benzoxazin-3-on-6-yl)propionate
and with "C" results in
  benzyl (2S)-2-[(R)-camphorsulfonamido]-3-{3,4-dihydro-2-[N-(2-benzimidazolylmethyl)carbamoylmethyl]-2H-1,4-benzoxazin-3-on-6-yl}propionate ("29").
Cleavage of the benzyl ester by hydrogenation affords from "27"
  (2S)-2-[(R)-camphorsulfonamido]-3-(3,4-dihydro-2-[N-(2-benzimidazolyl)carbamoylmethyl]-2H-1,4-benzox-azin-3-on-6-yl)propionic acid ("28"), FAB 624
and from "29"
  (2S)-2-[(R)-camphorsulfonamido]-3-{3,4-dihydro-2-[N-(2-benzimidazolylmethyl)carbamoylmethyl]-2H-1,4-benzoxazin-3-on-6-yl}propionic acid ("30"), FAB 638.
  Analogous reaction of benzyl (2S)-2-butylsulfonamido-3-(3,4-dihydro-2-carboxy-methyl-2H-1,4-benzoxazin-3-on-6-yl)propionate
with "A" results in
  benzyl (2S)-2-butylsulfonamido-3-{3,4-dihydro-2-[N-(2-benzimidazolyl)carbamoylmethyl]-2H-1,4-benzoxazin-3-on-6-yl}propionate,
with "B" results in
  benzyl (2S)-2-butylsulfonamido-3-{3,4-dihydro-2-[N-(2-imidazolyl)carbamoylmethyl]-2H-1,4-benzoxazin-3-on-6-yl}propionate,
with "C" results in
  benzyl (2S)-2-butylsulfonamido-3-{3,4-dihydro-2-[N-(2-benzimidazolylmethyl)carbamoylmethyl]-2H-1,4-benzoxazin-3-on-6-yl}propionate;
  of benzyl (2S)-2-(4-tolylsulfonamido)-3-(3,4-dihydro-2-carboxymethyl-2H-1,4-benzoxazin-3-on-6-yl)propionate
with "A" results in
  benzyl (2S)-2-(4-tolylsulfonamido)-3-{3,4-dihydro-2-[N-(2-benzimidazolyl)carbamoylmethyl]-2H-1,4-benzoxazin-3-on-6-yl}propionate,
with "B" results in
  benzyl (2S)-2-(4-tolylsulfonamido)-3-{3,4-dihydro-2-[N-(2-imidazolyl)carbamoylmethyl]-2H-1,4-benzoxazin-3-on-6-yl}propionate,
with "C" results in
  benzyl (2S)-2-(4-tolylsulfonamido)-3-{3,4-dihydro-2-[N-(2-benzimidazolylmethyl)carbamoylmethyl]-2H-1,4-benzoxazin-3-on-6-yl}propionate;
  of benzyl (2S)-2-benzylsulfonamido-3-(3,4-dihydro-2-carboxymethyl-2H-1,4-benzoxazin-3-on-6-yl)propionate
with "A" results in
  benzyl (2S)-2-benzylsulfonamido-3-{3,4-dihydro-2-[N-(2-benzimidazolyl)carbamoylmethyl]-2H-1,4-benzoxazin-3-on-6-yl}propionate,
with "B" results in
  benzyl (2S)-2-benzylsulfonamido-3-{3,4-dihydro-2-[N-(2-imidazolyl)carbamoylmethyl]-2H-1,4-benzoxazin-3-on-6-yl}propionate,
with "C" results in
  benzyl (2S)-2-benzylsulfonamido-3-{3,4-dihydro-2-[N-(2-benzimidazolylmethyl)carbamoylmethyl]-2H-1,4-benzoxazin-3-on-6-yl}propionate, of benzyl (2S)-2-phenylsulfonamido-3-(3,4-dihydro-2-carboxymethyl-2H-1,4-benzoxazin-3-on-6-yl)propionate
with "A" results in
  benzyl (2S)-2-phenylsulfonamido-3-{3,4-dihydro-2-[N-(2-benzimidazolyl)carbamoylmethyl]-2H-1,4-benzoxazin-3-on-6-yl}propionate,
with "B" results in
  benzyl (2S)-2-phenylsulfonamido-3-{3,4-dihydro-2-[N-(2-imidazolyl)carbamoylmethyl]-2H-1,4-benzoxazin-3-on-6-yl}propionate,
with "C" results in
  benzyl (2S)-2-phenylsulfonamido-3-{3,4-dihydro-2-[N-(2-benzimidazolylmethyl)carbamoylmethyl]-2H-1,4-benzoxazin-3-on-6-yl}propionate,
  of benzyl (2S)-2-(2-naphthylsulfonamido)-(3,4-dihydro-2-carboxymethyl-2H-1,4-benzoxazin-3-on-6-yl)propionate
  with "A" results in benzyl (2S)-2-(2-naphthylsulfonamido)-3-{3,4-dihydro-2-[N-(2-benzimidazolyl)carbamoylmethyl]-2H-1,4-benzoxazin-3-on-6-yl}propionate,
with "B" results in
  benzyl (2S)-2-(2-naphthylsulfonamido)-3-{3,4-dihydro-2-[N-(2-imidazolyl)carbamoylmethyl]-2H-1,4-benzoxazin-3-on-6-yl}propionate,
with "C" results in
  benzyl (2S)-2-(2-naphthylsulfonamido)-3-{3,4-dihydro-2-[N-(2-benzimidazolylmethyl)carbamoylmethyl]-2H-1,4-benzoxazin-3-on-6-yl}propionate;
  of benzyl (2S)-2-cyclohexylsulfonamido-3-(3,4-dihydro-2-carboxymethyl-2H-1,4-benzoxazin-3-on-6-yl)propionate
with "A" results in
  benzyl (2S)-2-cyclohexylsulfonamido-3-{3,4-dihydro-2-[N-(2-benzimidazolyl)carbamoylmethyl]-2H-1,4-benzoxazin-3-on-6-yl}propionate,
with "B" results in
  benzyl (2S)-2-cyclohexylsulfonamido-3-{3,4-dihydro-2-[N-(2-imidazolyl)carbamoylmethyl]-2H-1,4-benzoxazin-3-on-6-yl)propionate,
with "C" results in
  benzyl (2S)-2-cyclohexylsulfonamido-3-{3,4-dihydro-2-[N-(2-benzimidazolylmethyl)carbamoylmethyl]-2H-1,4-benzoxazin-3-on-6-yl}propionate.
Analogous cleavage of the last-mentioned benzyl esters by hydrogenation results in the following compounds
  (2S)-2-butylsulfonamido-3-{3,4-dihydro-2-[N-(2-benzimidazolyl)carbamoylmethyl]-2H-1,4-benzoxazin-3-on-6-yl}propionic acid;
  (2S)-2-butylsulfonamido-3-{3,4-dihydro-2-[N-(2-imidazolyl)carbamoylmethyl]-2H-1,4-benzoxazin-3-on-6-yl}propionic acid;
  (2S)-2-butylsulfonamido-3-{3,4-dihydro-2-[N-(2-benzimidazolylmethyl)carbamoylmethyl]-2H-1,4-benzoxazin-3-on-6-yl}propionic acid;
  (2S)-2-(4-tolylsulfonamido)-3-{3,4-dihydro-2-[N-(2-benzimidazolyl)carbamoylmethyl]-2H-1,4-benzoxazin-3-on-6-yl}propionic acid;
  (2S)-2-(4-tolylsulfonamido)-3-(3,4-dihydro-2-[N-(2-imidazolyl)carbamoylmethyl]-2H-1,4-benzoxazin-3-on-6-yl}propionic acid;
  (2S)-2-(4-tolylsulfonamido)-3-{3,4-dihydro-2-[N-(2-benzimidazolylmethyl)carbamoylmethyl]-2H-1,4-benzoxazin-3-on-6-yl}propionic acid;

(2S)-2-benzylsulfonamido-3-{3,4-dihydro-2-[N-(2-benzimidazolyl)carbamoylmethyl]-2H-1,4-benzoxazin-3-on-6-yl}propionic acid;
(2S)-2-benzylsulfonamido-3-{3,4-dihydro-2-[N-(2-imidazolyl)carbamoylmethyl]-2H-1,4-benzoxazin-3-on-6-yl}propionic acid;
(2S)-2-benzylsulfonamido-3-{3,4-dihydro-2-[N-(2-benzimidazolylmethyl)carbamoylmethyl]-2H-1,4-benzoxazin-3-on-6-yl}propionic acid;
(2S)-2-phenylsulfonamido-3-{3,4-dihydro-2-[N-(2-benzimidazolyl)carbamoylmethyl]-2H-1,4-benzoxazin-3-on-6-yl}propionic acid;
(2S)-2-phenylsulfonamido-3-{3,4-dihydro-2-[N-(2-imidazolyl)carbamoylmethyl]-2H-1,4-benzoxazin-3-on-6-yl}propionic acid;
(2S)-2-phenylgulfonamido-3-{3,4-dihydro-2-[N-(2-benzimidazolylmethyl)carbamoylmethyl]-2H-1,4-benzoxazin-3-on-6-yl}propionic acid;
(2S)-2-(2-naphthylsulfonamido)-3-{3,4-dihydro-2-[N-(2-benzimidazolyl)carbamoylmethyl]-2H-1,4-benzoxazin-3-on-6-yl}propionic acid;
(2S)-2-(2-naphthylsulfonamido)-3-{3,4-dihydro-2-[N-(2-imidazolyl)carbamoylmethyl]-2H-1,4-benzoxazin-3-on-6-yl}propionic acid;
(2S)-2-(2-naphthylsulfonamido)-3-{3,4-dihydro-2-[N-(2-benzimidazolylmethyl)carbamoylmethyl]-2H-1,4-benzoxazin-3-on-6-yl}propionic acid;
(2S)-2-cyclohexylsulfonamido-3-{3,4-dihydro-2-[N-(2-benzimidazolyl)carbamoylmethyl]-2H-1,4-benzoxazin-3-on-6-yl}propionic acid;
(2S)-2-cyclohexylsulfonamido-3-{3,4-dihydro-2-[N-(2-imidazolyl)carbamoylmethyl]-2H-1,4-benzoxazin-3-on-6-yl}propionic acid;
(2S)-2-cyclohexylsulfonamido-3-{3,4-dihydro-2-[N-(2-benzimidazolylmethyl)carbamoylmethyl]-2H-1,4-benzoxazin-3-on-6-yl}propionic acid;

EXAMPLE 7

Elimination of the BOC group with TFA in dichloromethane affords
from "19"
benzyl (2S)-2-amino-3-{3,4-dihydro-2-[N-(2-benzimidazolyl)carbamoylmethyl]-2H-1,4-benzoxazin-3-on-6-yl}propionate ("31a"), FAB 500;
from "20"
benzyl (2S)-2-amino-3-{3,4-dihydro-2-[N-(2-imidazolyl)carbamoylmethyl]-2H-1,4-benzoxazin-3-on-6-yl}propionate ("31b")
and from "21"
benzyl (2S)-2-amino-3-{3,4-dihydro-2-[N-(2-benzimidazolylmethyl)carbamoylmethyl]-2H-1,4-benzoxazin-3-on-6-yl}propionate ("31c").

22 μl of butylsulfonyl chloride ("D") and 71 μl of triethylamine are added to a solution of 0.13 g of "31a" in 15 ml of dichloromethane and stirred for 30 hours. The crude product after the usual workup is hydrogenated in analogy to Example 1. Purification by preparative HPLC results in 13 mg of (2S)-2-butylsulfonamido-3-{3,4-dihydro-2-[N-(2-benzimidazol-yl)carbamoylmethyl]-2H-1,4-benzoxazin-3-on-6-yl}propionic acid ("32a"), FAB 530;
analogous reaction of "D" and subsequent hydrogenation with "31b" result in
(2S)-2-butylsulfonamido-3-{3,4-dihydro-2-[N-(2-imidazolyl)carbamoylmethyl]-2H-1,4-benzoxazin-3-on-6-yl}propionic acid ("32b")
and with "31c" result in
(2S)-2-butylsulfonamido-3-{3,4-dihydro-2-[N-(2-benzimidazolylmethyl)carbamoylmethyl]-2H-1,4-benzoxazin-3-on-6-yl}propionic acid ("32c").

EXAMPLE 8

A solution of 2.1 g of "1", 3.7 g of diethyl 2,4-dibromoadipate, 1.4 g of potassium carbonate and 0.137 g of 18-crown-6 in 100 ml of toluene is stirred at 80° for 2 hours. The usual workup results in 1.8 g of benzyl (2S)-2-tert-butyloxycarboxamido-3-[3-nitro-4-(1,4-bis(ethoxycarbonyl)-4-bromobutyloxy)phenyl]propionate ("34") as a colourless syrup, FAB 696.

A solution of 1.5 g of "34" and 0.7 g of sodium azide in 60 ml of DMF is stirred at 60° for 12 hours. The usual workup results in 1.3 g of benzyl (2S)-2-tert-butyloxycarboxamido-3-[3-nitro-4-(1,4-bis(ethoxycarbonyl)-4-azidobutyloxy)phenyl]propionate ("35"), FAB 658.

1.1 g of "35" are dissolved in 50 ml of methanol and, after addition of 5.9 ml of 1N NaOH, stirred for 5 hours. The usual workup results in 0.85 g of (2S)-2-tert-butyloxycarboxamido-3-[3-nitro-4-(1,4-biscarboxy-4-azidobutyloxy)phenyl]propionic acid ("36"), FAB 512.

A solution of 0.5 g of "36" in 10 ml of dioxane and 5 ml of water is hydrogenated in the presence of 0.1 g of palladium (10% on active carbon) for 6 hours. The pH is kept at between 4 and 6 with 1N HCl. Removal of the catalyst and the solvents results in 0.21 g of (2S)-2-tert-butyloxycarboxamido-3-[3,4-dihydro-2-(3-amino-3-carboxypropyl)-2H-1,4-benzoxazin-3-on-6-yl]propionic acid ("37"), FAB 456.

The crude product "37" (0.2 g) is dissolved in 10 ml of DMF, 2 ml of ethanol and 1 ml of water and guanylated with 0.354 g of DPFN in the presence of 0.5 ml of triethylamin at 60° for 24 hours. The usual workup results in 0.1 g of (2S)-2-tert-butyloxycarboxamido-3-[3,4-dihydro-2-(3-guanidino-3-carboxypropyl)-2H-1,4-benzoxazin-3-on-6-yl]-propionic acid ("38"), FAB480.

32 mg of 2-chloro-1-methylpyridinium iodide and 60 μl of ethyldiisopropylamine are added to a solution of 50 mg of "38" (trifluoroacetate) in 2 ml of DMF and stirred for 12 hours. The usual workup results in 22 mg of (2S)-2-tert-butyloxycarboxamido-3-{3,4-dihydro-2-[3-(2-imino-4-oxoimidazolidin-5-yl)propyl]-2H-1,4-benzoxazin-3-on-6-yl}propionic acid ("39").

EXAMPLE 9

Equimolar amounts of tert-butyl bromoacetate and NaH are added to a solution of benzyl (2S)-2-butylsulfonamido-3-(3-hydroxymethyl-1,4-benzodioxan-6-yl)propionate in DMF. The mixture is stirred for 2 hours, and the usual workup results in benzyl 2-butylsulfonamido-3-(2-tert-butoxycarbonylmethoxymethyl-1,4-benzodioxan-6-yl)propionate.

Analogously, subsequent elimination of the BOC group with TFA, reaction with 2-aminobenzimidazole and cleavage of the benzyl ester by hydrogenation result in the compound (2S)-2-butylsulfonamido-3-{2-[(1H-imidazol-2-ylcarbamoyl)methoxymethyl]-1,4-benzodioxan-6-yl}propionic acid.

2-(4-Tolylsulfonamido)-3-{2-[(1H-imidazol-2-ylcarbamoyl)methoxymethyl]-1,4-benzodioxan-6-yl}propionic acid is obtained analogously.

EXAMPLE 10

Reaction of "25" with 2,2,2-trichloro-1,1-dimethylethyl chloroformate and subsequent cleavage of the benzyl ester by hydrogenation results in the compound (2S)-2-{[(2,2,2- trichloro-1,1-dimethyl)ethyl]-carboxamido}-3-(3,4-dihydro-2-carboxymethyl-2H-1,4-benzoxazin-3-on-6-yl)propionic acid ("40").

Reaction in analogy to Example 5 of "40" with "A" affords the compound (2S)-2-{[(2,2,2-trichloro-1,1-dimethyl)ethyloxy]carboxamido}-3-{3,4-dihydro-2-[N-(2-benzimidazolyl)carbamoylmethyl]-2H-1,4-benzoxazin-3-on-6-yl}propionic acid, trifluoroacetate, FAB 726

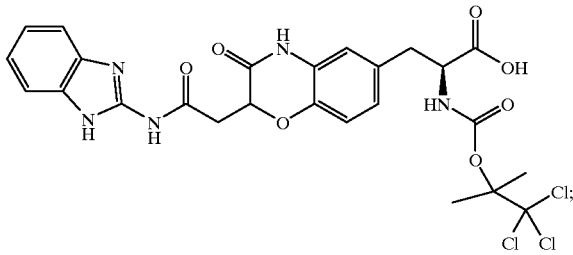

The compound (2S)-2-{[(neopentyloxy)ethyl]carboxamido}-3-(3,4-dihydro-2-[N-(2-benzimidazoyl)carbamoylmethyl]-2H-1,4-benzoxazin-3-on-6-yl}propionic acid, FAB 524, is obtained analogously.

EXAMPLE 11

Reaction of BOC-3-amino-L-tyrosine ethyl ester with (2S)-bromopentanedioic acid 5-benzyl ester [obtainable by reacting L-glutamic acid γ-benzyl ester with NaNO$_2$ and KBr in sulfuric acid], and EDC1 in dichloromethane at room temperature results, after stirring for 12 hours and the usual workup, in the compound benzyl (4S)-4-bromo-4-[5-((2S)-2-tert-butyloxycarbonylamino-2-ethoxycarbonylethyl)-2-hydroxyphenylcarbamoyl]butyrate, FAB 608.

Heating with DBU (diazabicycloundec-7-ene) in toluene at 100° for 12 hours results, after the usual workup, in the compound ethyl (2S)-3-[(2R)-2-(2-benzyloxycarbonylethyl)-3-oxo-3,4-dihydro-2H-benzo[1,4]oxazin-6-yl]-2--tert-butoxycarbonylaminopropionate, FAB 527. Hydrogenation with Pd/C results in ethyl (2S)-2-tert-butoxycarbonylamino-3-[(2R)-2-(2-carboxyethyl)-3-oxo-3,4-dihydro-2H-benzo[1,4]oxazin-6-yl]propionate ("41"), FAB 437

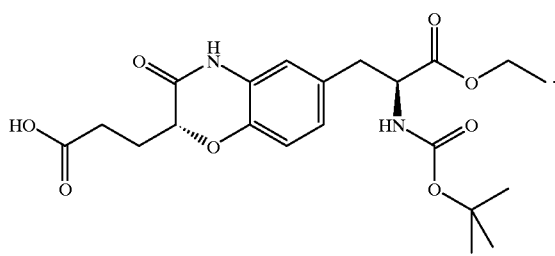

Reaction in analogy to Example 5 of "41" with "A" results in
ethyl (2S)-2-tert-butyloxycarboxamido-3-{3,4-dihydro-2-[N-(2-benzimidazolyl)carbamoylethyl]-(2R)-2H-1,4-benzoxazin-3-on-6-yl}propionate ("42") and
with "B" results in
ethyl (2S)-2-tert-butyloxycarboxamido-3-{3,4-dihydro-2-[N-(2-imidazolyl)carbamoylethyl]-(2R)-2H-1,4-benzoxazin-3-on-6-yl}propionate ("43"), FAB 502.

Cleavage of the ethyl ester in "42" and "43" with aqueous NaOH results in the compounds (2S)-2-tert-butyloxycarboxamido-3-{3,4-dihydro-2-[N-(2-benzimidazolyl)carbamoylethyl]-(2R)-2H-1,4-benzoxazin-3-on-6-yl}propionic acid, FAB 524 and
(2S)-2-tert-butyloxycarboxamido-3-{3,4-dihydro-2-[N-(2-imidazolyl)carbamoylethyl]-(2R)-2H-1,4-benzoxazin-3-on-6-yl}propionic acid, FAB 474.

The following compound is obtained analogously
(2S)-2-tert-butyloxycarboxamido-3-{3,4-dihydro-2-[N-(2-imidazolyl)carbamoylethyl]-(2S)-2H-1,4-benzoxazin-3-on-6-yl}propionic acid, FAB 474.

EXAMPLE 12

Elimination of the BOC group from "42" and "43" with TFA in dichloromethane results in the following compounds
ethyl (2S)-2-amino-3-{3,4-dihydro-2-[N-(2-benzimidazolyl)carbamoylethyl]-(2R)-2H-1,4-benzoxazin-3-on-6-yl}propionate ("44") and
ethyl (2S)-2-amino-3-{3,4-dihydro-2-[N-(2-imidazolyl)carbamoylethyl]-(2R)-2H-1,4-benzoxazin-3-on-6-yl}propionate ("45"), FAD 402.

Reaction in analogy to Example 6 of "44"
with 2,3,5,G-tetramethylsulfonyl chloride results in
ethyl (2S)-2-(2,3,5,6-tetramethylphenylsulfonamido)-3-{3,4-dihydro-2-[N-(2-benzimidazolyl)carbamoylethyl]-(2R)-2H-1,4-benzoxazin-3-on-6-yl}propionate
and ester cleavage thereof results in
(2S)-2-(2,3,5,6-tetramethylphenylsulfonamido)-3-{3,4-dihydro-2-[N-(2-benzimidazolyl)carbamoylethyl]-(2R)-2H-1,4-benzoxazin-3-on-6-yl}propionic acid, FAB 620.

Analogous reaction of "45"
with 3-chloro-6-methoxyphenylsulfonyl chloride results in
ethyl (2S)-2-(3-chloro-6-methoxyphenylsulfonamido)-3-{3,4-dihydro-2-[N-(2-imidazolyl)carbamoylethyl]-(2R)-2H-1,4-benzoxazin-3-on-6-yl}propionate,
with 1-naphthylsulfonyl chloride results in
ethyl (2S)-2-(1-naphthylsulfonamido)-3-{3,4-dihydro-2-[N-(2-imidazolyl)carbamoylethyl]-(2R)-2H-1,4-benzoxazin-3-on-6-yl}propionate,
with 2,3,5,6-tetramethylphenylsulfonyl chloride results in
ethyl (2S)-2-(2,3,5,6-tetramethylphenylsulfonamido)-3-{3,4-dihydro-2-[N-(2-imidazolyl)carbamoylethyl]-(2R)-2H-1,4-benzoxazin-3-on-6-yl}propionate,
with (R)-camphor-10-sulfonyl chloride results in
ethyl (2S)-2-[(R)-camphor-10-sulfonamido]-3-{3,4-dihydro-2-[N-(2-imidazolyl)carbamoylethyl]-(2R)-2H-1,4-benzoxazin-3-on-6-yl}propionate,
with butylsulfonyl chloride results in
ethyl (2S)-2-butylsulfonamido-3-{3,4-dihydro-2-[N-(2-imidazolyl)carbamoylethyl]-(2R)-2H-1,4-benzoxazin-3-on-6-yl}propionate,
with isopropyl chloroformate results in
ethyl (2S)-2-isopropoxycarboxamido-3-{3,4-dihydro-2-[N-(2-imidazolyl)carbamoylethyl]-(2R)-2H-1,4-benzoxazin-3-on-6-yl}propionate,
with isobutyl chloroformate results in
ethyl (2S)-2-isobutoxycarboxamido-3-{3,4-dihydro-2-[N-(2-imidazolyl)carbamoylethyl]-(2R)-2H-1,4-benzoxazin-3-on-6-yl}propionate,
with neopentyl chloroformate results in
ethyl (2S)-2-neopentyloxycarboxamido-3-{3,4-dihydro-2-[N-(2-imidazolyl)carbamoylethyl]-(2R)-2H-1,4-benzoxazin-3-on-6-yl}propionate,
with benzyl chloroformate results in
ethyl (2S)-2-benzyloxycarboxamido-3-{3,4-dihydro-2-[N-(2-imidazolyl)carbamoylethyl]-(2R)-2H-1,4-benzoxazin-3-on-6-yl}propionate, with benzylsulfonyl chloride results in ethyl (2S)-2-benzylsulfonamido-3-{3,4-dihydro-2-[N-(2-imidazolyl)carbamoylethyl]-(2R)-2H-1,4-benzoxazin-3-on-6-yl}propionate, and ester cleavage thereof results in the following propionic acid derivatives (2S)-2-(3-chloro-6-methoxyphenylsulfonamido)-3-{3,4-dihydro-2-[N-(2-imidazolyl)carbamoylethyl]-(2R)-2H-1,4-benzoxazin-3-on-6-yl}propionic acid, FAB 578;

(2S)-2-(1-naphthylsulfonamido)-3-{3,4-dihydro-2-[N-(2-imidazolyl)carbamoylethyl]-(2R)-2H-1,4-benzoxzin-3-on-6-yl}propionic acid, FAB 564;

(2S)-2-(2,3,5,6-tetramethylphenylsulfonamido)-3-{3,4-dihydro-2-[N-(2-imidazolyl)carbamoylethyl]-(2R)-2H-1,4-benzoxazin-3-on-6-yl}propionic acid, FAB 570;

(2S)-2-[(R)-camphor-10-sulfonamido]-3-{3,4-dihydro-2-[N-(2-imidazolyl)carbamoylethyl]-(2R)-2H-1,4-benzoxazin-3-on-6-yl}propionic acid, FAB 588;

(2S)-2-butylsulfonamido-3-{3,4-dihydro-2-[N-(2-imidazolyl) carbamoylethyl]-(2R)-2H-1,4-benzoxazin-3-on-6-yl}propionic acid, FAB 494;

(2S)-2-isopropoxycarboxamido-3-{3,4-dihydro-2-[N-(2-imidazolyl)carbamoylethyl]-(2R)-2H-1,4-benzoxazin-3-on-6-yl}propionic acid, FAB 460;

(2S)-2-isobutoxycarboxamido-3-{3,4-dihydro-2-[N-(2-imidazolyl) carbamoylethyl]-(2R) -2H-1,4-benzoxazin-3-on-6-yl}propionic acid, FAB 474;

(2S)-2-neopentyloxycarboxamido-3-{3,4-dihydro-2-[N-(2-imidazolyl)carbamoylethyl]-(2R)-2H-1,4-benzoxazin-3-on-6-yl}propionic acid, FAB 488;

(2S)-2-benzyloxycarboxamido-3-{3,4-dihydro-2-[N-(2-imidazolyl)carbamoylethyl]-(2R)-2H-1,4-benzoxazin-3-n-6-yl}propionic acid, FAB 508;

(2S)-2-benzylsulfonamido-3-{3,4-dihydro-2-[N-(2-imidazolyl)carbamoylethyl]-(2R)-2H-1,4-benzoxazin-3-on-6-yl}propionic acid, FAB 528;

(2S)-2-benzenesulfonamido-3-{3,4-dihydro-2-[N-(2-imidazolyl)carbamoylethyl]-(2R)-2H-1,4-benzoxazin-3-on-6-yl}propionic acid, FAB 514.

The compound (2S)-2-(1,1-dimethyl-2,2,2-trichloroethyloxycarboxamido)-3-{3,4-dihydro-2-[N-(2-imidazolyl)-carbamoylethyl]-(2R)-2H-1,4-benzoxazin-3-on-6-yl}-propionic acid, FAB 578, is obtained analogously.

EXAMPLE 13

25 g of L-Orn(N$^\delta$-Z) are dissolved together with 37 g of potassium bromide in 300 l of 2.5 N sulfuric acid and, at 0°, 9.7 g of sodium nitrite are added. The mixture is allowed to warm to room temperature and then stirred for 12 hours. The usual workup results in 11 g of (2S)-2-bromo-4-benzyloxycarbonylaminobutyric acid as oil, EI 330.

Subsequent reaction with BOC-3-amino-L-tyrosine ethyl ester and EDCl in dichloromethane at room temperature results, after stirring for 12 hours, the usual workup and subsequent reaction of the product with DBU (diazabicycloundec-7-ene) in toluene at 100°, in the compound ethyl (2S)-3-[(2R)-2-(3-benzyloxycarbonylaminopropyl)-3-oxo-3,4-dihydro-2H-benzo[1,4]oxazin-6-yl]-2-tert-butoxycarbonylaminopropionate ("46"), FAB 556.

Ester hydrolysis with aqueous sodium hydroxide solution and subsequent elimination of the Z group by hydrogenation (Pd/C) in dioxane/water results in the compound (2S)-3-[(2R)-2-(3-aminopropyl)-3-oxo-3,4-dihydro-2H-benzo[1,4]oxazin-6-yl]-2-tert-butoxycarbonylamino-propionic acid, FAB 394.

Reaction in analogy to Example 3 thereof with DPFN results in the compound (2S)-3-[(2R)-2-(3-guanidinopropyl)-3-oxo-3,4-dihydro-2H-benzo[1,4]oxazin-6-yl]-2-tert-butoxycarbonylaminopropionic acid, FAB 436.

Elimination of the BOC group from "46" with TFA in dichloromethane results in the compound ethyl (2S)-2-amino-3-[(2R)-2-(3-benzyloxycarbonylaminopropyl)-3-oxo-3,4-dihydro-2H-benzo[1,4]oxazin-6-yl]propionate ("47"), trifluoroacetate, FAB 456

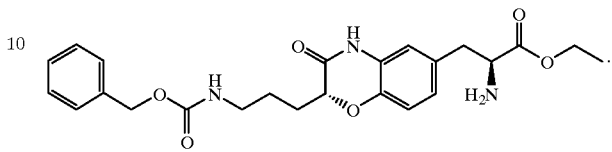

Reaction in analogy to Example 6 of "47"
with 2,3,5,6-tetramethylphenylsulfonyl chloride results in
ethyl (2S)-2-(2,3,5,6-tetramethylphenylsulfonamido)-3-{3,4-dihydro-2-(3-benzyloxycarbonylaminopropyl)-(2R)-2H-1,4-benzoxazin-3-on-6-yl}propionate,
with 3-chloro-6-methoxyphenylsulfonyl chloride results in
ethyl (2S)-2-(3-chloro-6-methoxyphenylsulfonamido)-3-{3,4-dihydro-2-(3-benzyloxycarbonylaminopropyl)-(2R)-2H-1,4-benzoxazin-3-on-6-yl}propionate,
with 1-naphthylsulfonyl chloride results in
ethyl (2S)-2-(1-naphthylsulfonamido)-3-{3,4-dihydro-2-(3-benzyloxycarbonylaminopropyl)-(2R)-2H-1,4-benzoxazin-3-on-6-yl}propionate,
with 2,3,5,6-tetramethylphenylsulfonyl chloride results in
ethyl (2S)-2-(2,3,5,6-tetramethylphenylsulfonamido)-3-{3,4-dihydro-2-(3-benzyloxycarbonylaminopropyl)-(2R)-2H-1,4-benzoxazin-3-on-6-yl}propionate,
with (R)-camphor-10-sulfonyl chloride results in
ethyl (2S)-2-[(R)-camphor-10-sulfonamido]-3-{3,4-dihydro-2-(3-benzyloxycarbonylaminopropyl)-(2R) -2H-1,4-benzoxazin-3-on-6-yl}propionate,
with butylsulfonyl chloride results in
ethyl (2S) -2-butylsulfonamido-3-{3,4-dihydro-2-(3-benzyloxycarbonylaminopropyl)-(2R)-2H-1, 4-benzoxazin-3-on-6-yl}propionate, FAB 576;
with isopropyl chloroformate results in
ethyl (2S)-2-isopropoxycarboxamido-3-{3,4-dihydro-2-(3-benzyloxycarbonylaminopropyl)-(2R)-2H-1,4-benzoxazin-3-on-6-yl}propionate,
with isobutyl chloroformate results in
ethyl (2S)-2-isobutoxycarboxamido-3-{3,4-dihydro-2-(3-benzyloxycarbonylaminopropyl)-(2R)-2H-1,4-benzoxazin-3-on-6-yl}propionate,
with neopentyl chloroformate results in
ethyl (2S)-2-neopentyloxycarboxamido-3-{3,4-dihydro-2-(3-benzyloxycarbonylaminopropyl)-(2R)-2H-1,4-benzoxazin-3-on-6-yl}propionate, FAB 570;
with benzyl chloroformate results in
ethyl (2S)-2-benzyloxycarboxamido-3-{3,4-dihydro-2-(3-benzyloxycarbonylaminopropyl)-(2R)-2H-1,4-benzoxazin-3-on-6-yl}propionate,
with benzylsulfonyl chloride results in
ethyl (2S) -2-benzylsulfonamido-3-{3,4-dihydro-2-(3-benzyloxycarbonylaminopropyl)-(2R)-2H-1,4-benzoxazin-3-on-6-yl}propionate,
with benzenesulfonyl chloride results in
ethyl (2S) -2-benzenesulfonamido-3-{3,4-dihydro-2-(3-benzyloxycarbonylaminopropyl)-(2R)-2H-1,4-benzoxazin-3-on-6-yl}propionate.

Ester cleavage and hydrogenation of the above-mentioned Z-protected propionates result in the following compounds
(2S)-2-(2,3,5,6-tetramethylphenylsulfonamido)-3-{3,4-dihydro-2-(3-aminopropyl)-(2R)-2H-1,4-benzoxazin-3-on-6-yl}propionic acid, (2S)-2-(3-chloro-6-methoxyphenylsulfonamido)-3-{3,4-dihydro-2-(3-aminopropyl)-(2R)-2H-1,4-benzoxazin-3-on-6-yl}propionic acid,
(2S)-2-(l-naphthylsulfonamido)-3-{3,4-dihydro-2-(3-aminopropyl)-(2R)-2H-1,4-benzoxazin-3-on-6-yl}propionic acid,
(2S)-2-(2,3,5,6-tetramethylphenylsulfonamido)-3-{3,4-dihydro-2-(3-aminopropyl)-(2R)-2H-1,4-benzoxazin-3-on-6-yl}propionic acid,
(2S)-2-[(R)-camphor-10-sulfonamido]-3-{3,4-dihydro-2-(3-aminopropyl)-(2R)-2H-1,4-benzoxazin-3-on-6-yl}propionic acid,
(2S)-2-butylsulfonamido-3-{3,4-dihydro-2-(3-aminopropyl)-(2R)-2H-1,4-benzoxazin-3-on-6-yl}propionic acid,
(2S)-2-isopropoxycarboxamido-3-{3,4-dihydro-2-(3-aminopropyl)-(2R)-2H-1,4-benzoxazin-3-on-6-yl}propionic acid,
(2S)-2-isobutoxycarboxamido-3-{3,4-dihydro-2-(3-aminopropyl)-(2R)-2H-1,4-benzoxazin-3-on-6-yl}propionic acid,
(2S)-2-neopentyloxycarboxamido-3-{3,4-dihydro-2-(3-aminopropyl)-(2R)-2H-1,4-benzoxazin-3-on-6-yl}propionic acid, FAB 408;
(2S)-2-benzyloxycarboxamido-3-{3,4-dihydro-2-(3-aminopropyl)-(2R)-2H-1,4-benzoxazin-3-on-6-yl}propionic acid,
(2S)-2-benzylsulfonamido-3-{3,4-dihydro-2-(3-aminopropyl)-(2R)-2H-1,4-benzoxazin-3-on-6-yl}propionic acid,
(2S)-2-benzenesulfonamido-3-{3,4-dihydro-2-(3-aminopropyl)-(2R)-2H-1,4-benzoxazin-3-on-6-yl}propionic acid.

Reaction in analogy to Example 3 of the above-mentioned propionic acids with DPFN results in the following compounds:

(2S)-2-(2,3,5,6-tetramethylphenylsulfonamido)-3-{3,4-dihydro-2-(3-guanidinopropyl)-(2R)-2H-1,4-benzoxazin-3-on-6-yl}propionic acid,
(2S)-2-(3-chloro-6-methoxyphenylsulfonamido)-3-{3,4-dihydro-2-(3-guanidinopropyl)-(2R)-2H-1,4-benzoxazin-3-on-5-yl}propionic acid,
(2S)-2-(1-naphthylsulfonamido)-3-{3,4-dihydro-2-(3-guanidinopropyl)-(2R)-2H-1,4-benzoxazin-3-on-6-yl}-propionic acid,
(2S)-2-(2,3,5,6-tetramethylphenylsulfonamido)-3-{3,4-dihydro-2-(3-guanidinopropyl)-(2R)-2H-1,4-benzoxazin-3-on-6-yl}propionic acid,
(2S)-2-[(R)-camphor-10-sulfonamido]-3-{3,4-dihydro-2-(3-guanidinopropyl)-(2R)-2H-1,4-benzoxazin-3-on-6-yl}propionic acid,
(2S)-2-butylsulfonamido-3-{3,4-dihydro-2-(3-guanidinopropyl)-(2R)-2H-1,4-benzoxazin-3-on-6-yl}propionic acid, FAB 456;
(2S)-2-isopropoxycarboxamido-3-{3,4-dihydro-2-(3-guanidinopropyl)-(2R)-2H-1,4-benzoxazin-3-on-6-yl}-propionic acid,
(2S)-2-isobutoxycarboxamido-3-{3,4-dihydro-2-(3-guanidinopropyl)-(2R)-2H-1,4-benzoxazin-3-on-6-yl}-propionic acid,
(2S)-2-neopentyloxycarboxamido-3-{3,4-dihydro-2-(3-guanidinopropyl)-(2R)-2H-1,4-benzoxazin-3-on-6-yl}-propionic acid, FAB 450;
(2S)-2-benzyloxycarboxamido-3-{3,4-dihydro-2-(3-guanidinopropyl)-(2R)-2H-1,4-benzoxazin-3-on-6-yl}-propionic acid,
(2S)-2-benzylsulfonamido-3-{3,4-dihydro-2-(3-guanidinopropyl)-(2R)-2H-1,4-benzoxazin-3-on-6-yl}propionic acid and
(2S)-2-benzenesulfonamido-3-{3,4-dihydro-2-(3-guanidinopropyl)-(2R)-2H-1,4-benzoxazin-3-on-6-yl}propionic acid.

The following examples relate to pharmaceutical compositions:

Example A: Vials

A solution of 100 g of an active substance of the formula I and 5 g of disodium hydrogen phosphate in 3 l of double-distilled water is adjusted to pH 6.5 with 2N hydrochloric acid, sterilized by filtration, dispensed into vials, lyophilized under sterile conditions and sealed sterile. Each vial contains 5 mg of active substance.

Example B: Suppositories

A mixture of 20 g of an active substance of the formula I with 100 g of soya lecithin and 1400 g of cocoa butter is melted, poured into moulds and left to cool. Each suppository contains 20 mg of active substance.

Example C: Solution

A solution is prepared from 1 g of an active substance of the formula I, 9.38 g of $NaH_2PO_4.2H_2O$, 28.48 g of $Na_2HPO_4.12H_2O$ and 0.1 g of benzalkonium chloride in 940 ml of double-distilled water. The pH is adjusted to 6.8, the volume is made up to 1 l, and the solution is radiation-sterilized. This solution can be used in the form of eye drops.

Example D: Ointment 500 mg of an active substance of the formula I are mixed with 99.5 g of petrolatum under aseptic conditions.

Example E: Tablets

A mixture of 1 kg of active substance of the formula I, 4 kg of lactose, 1.2 kg of potato starch, 0.2 kg of talc and 0.1 kg of magnesium stearate is compressed to tablets in a conventional way so that each tablet contains 10 mg of active substance.

Example F: Coated tablets

Tablets are compressed in analogy to Example E and then provided with a coating of sucrose, potato starch, talc, tragacanth and dye in a conventional way.

Example G: Capsules 2 kg of active substance of the formula I are packed into hard gelatin capsules in a conventional way so that each capsule contains 20 mg of the active substance.

Example E: Ampoules

A solution of 1 kg of active substance of the formula I in 60 l of double-distilled water is sterilized by filtration, dispensed into ampoules, lyophilized under sterile conditions and sealed sterile. Each ampoule contains 10 mg of active substance.

Example I: Inhalation Spray 14 g of active substance of the formula I are dissolved in 10 l of isotonic NaCl solution, and the solution is dispensed into commercially available spraying vessels with a pump mechanism. The solution can be sprayed into the mouth or nose. One puff (about 0.1 ml) corresponds to a dose of about 0.14 mg.

What is claimed is:

1. A compound of formula I

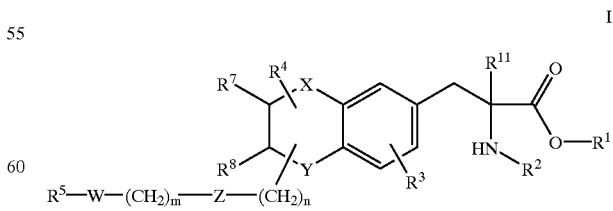

wherein $R^1$ is H, alkyl having 1–6 c atoms or benzyl,
$R^2$ is $R^{10}$, CO—$R^{10}$, $COOR^6$, $COOR^{10}$, $SO_2R^6$ or $SO_2R^{10}$, $R^3$ is H, Hal, OA, NHR$^{10}$, N(R$^{10}$)$_2$, —NH-acyl, —O-acyl, CN, NO$_2$, OR$^{10}$, SR$^{10}$, R$^2$ or CONHR$^{10}$, $R^4$ is H, =O, =S, C$_1$–C$_6$-alkyl or acyl, $R^5$ is NH$_2$, H$_2$N—C(=NH) or H$_2$N—(C=NH)—NH, where the primary amino groups can also be provided with conventional amino protective groups or can be mono-, di- or trisubstituted by R$^{10}$, CO—R$^{10}$, COOR$^{10}$ or SO$_2$R$^{10}$, or R$^6$, $R^7$, $R^8$ are each independently of one another absent or H, $R^7$ and $R^8$ together are also a bond, X, Y are each independently of one another =N—, —N—, O, S, —CH$_2$— or =C—, with the proviso that at least one of the two definitions X, Y is =N—, —N—, O or S, W, Z are each independently of one another absent, O, S, NR$^1$, C(=O), CONH, NHCO, C(=S)NH, NHC(S), C(=S), SO$_2$NH, NHSO$_2$ or CA=CA', $R^6$ is a mono- or binuclear heterocyclic which has 1 to 4 N, O and/or S atoms and can be unsubstituted or mono-, di or trisubstituted by Hal, A, —CO—A, OH, CN, COOH, COOA, CONH$_2$, NO$_2$, =NH or =O, $R^9$ is H, Hal, OA, NHA, NAA', NHacyl, Oacyl, CN, NO$_2$, SA, SOA, SO$_2$A, SO$_2$Ar or SO$_3$H, $R^{10}$ is H, A, Ar or aralkyl having 7–14 C atoms, $R^{11}$ is H or alkyl having 1–6 C atoms, A,A' are each independently of one another H or unsubstituted or mono-, di- or tri-R$^9$-substituted alkyl or cycloalkyl, each of which has 1–15 C atoms and in which one, two or three methylene groups can be replaced by N, O and/or S, Ar is unsubstituted or mono-, di or tri-A-and/or R$^9$-substituted mono- or binuclear aromatic ring system having 0, 1, 2, 3 or 4 N, O and/or S atoms, Hal is F, Cl, Br or I and m,n are each independently of one another 0, 1, 2, 3 or 4, an enantiomer or diastereomer thereof, or a physiologically acceptable salt thereof.

2. An enantiomer or diastereomer of a compound of formula I according to claim 1.

3. A compound of the formula I according to claim 1, which is a) (2S)-2-benzyloxycarboxamido-3-(2-guanidinomethyl-1,4-benzodioxan-6-yl)propionic acid;

b) (2S)-2-tert-butyloxycarboxamido-3-[3,4-dihydro-2-(2-guanidono-2-oxoethyl)2H-1,4-benzoxazin-3-on-6-yl]propionic acid;

c) (2S)-2-benzyloxycarboxamido-3-(2-guanidinoacetamidomethyl-1,4-benzodioxan-6-yl)propionic acid;

d) (2S)-2-tert-butyloxycarboxamido-3-{3,4-dihydro-2-[N-(2-imidazolyl)carbamoylmethyl]-2H-1,4-benzoxazin-3-on-6-yl)propionic acid;

e) (2S)-2-tert-butyloxycarboxcamido-3-{3,4-dihydro-2-[N-(2-benzimidazolyl)carbamoylmethyl]-2H-1,4-benzoxazin-3-on-6-yl)propioninc acid;

f) (2S)-2-tert-butyloxycarboxamido-3-{3,4-dihydro-2-[2-(2-imino-4-oxoimidzolidin-5-yl)ethyl]-2H-1,4-benzoxazin-3-on-6-yl}propionic acid;

g) (2S)-2-benzyloxycarboxamido-3-(2-(2R,S)-guanidinomethyl-1,4benzodioxan-6-yl)propionic acid.

4. A process for the preparation of a compound of formula 1 according to claim 1 or a salt thereof, comprising a) liberating a compound of formula from one of its functional derivatives by treatment with a solvolysing or hydrogenolysing agent, or b) reacting a compound of the formula II

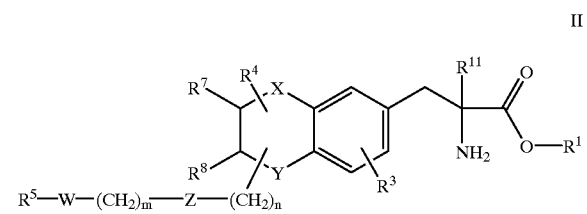

in which $R^1$, $R^3$, $R^4$, $R^5$, $R^7$, $R^8$, $R^{11}$, W, X, Y, Z, m and n have meanings stated in claim 1, with a compound of formula III $R^2$—L                III in which $R^2$ has the meaning stated in claim 1, and L is Cl, Br, I, OH or a reactively esterified OH group, or c) hydrolyzing an ester of the formula I, or d) converting a radical $R^1$ and/or $R^5$ into another radical $R^1$ and/or $R^5$, and/or e) converting into a pharmaceutically acceptable salt of a compound of formula I.

5. A process for the production of a pharmaceutical composition, comprising converting a compound of formula I according to claim 1 and/or one of its physiologically acceptable salts together with at least one solid, liquid or semiliquid excipient or ancillary substance.

6. A pharmaceutical composition comprising at least one compound of formula I according to claim 1 and/or a physiologically acceptable salt thereof, and a pharmaceutically acceptable excipient.

7. A method for treating thrombosis, myocardial infarct, coronary heart disease, or arteriosclerosis, comprising administering to a subject in need thereof an effective amount of a compound of claim 1.

8. A method of claim 7, wherein said compound is a GPIIb/IIIa antagonist.

9. A method for treating angiogenic disorders, tumors, osteoporosis, inflammation and infection, comprising administering to a subject in need thereof an effective amount of a compound of claim 1.

10. A method of claims 9, where said compound is a $\alpha_v$ integrin inhibitor.

11. A method for treating angiogenic disorders, thrombosis, mycardial infarct, coronary heart disease, arteriosclerosis, tumors, osteoporosis, inflammation, and infection, comprising administering to a subject in need thereof an effective amount of a compound of claim 1, wherein $R^2$ is camphor-10-yl.

12. A method of claim 11, wherein said compound is an $\alpha_v$ integrin inhibitor.

* * * * *